(12) United States Patent
Lardy et al.

(10) Patent No.: US 7,550,450 B2
(45) Date of Patent: *Jun. 23, 2009

(54) PROSTATE CANCER TREATMENT

(75) Inventors: Henry A. Lardy, Madison, WI (US);
Ashok Marwah, Middleton, WI (US);
Padma Marwah, Middleton, WI (US)

(73) Assignee: Hollis-Eden Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/862,153

(22) Filed: Sep. 26, 2007

(65) Prior Publication Data

US 2008/0070881 A1 Mar. 20, 2008

Related U.S. Application Data

(62) Division of application No. 10/814,503, filed on Mar. 30, 2004, now abandoned.

(60) Provisional application No. 60/459,450, filed on Apr. 1, 2003.

(51) Int. Cl.
*A61K 31/58* (2006.01)
(52) U.S. Cl. .................................... 514/173
(58) Field of Classification Search ................. 514/173
See application file for complete search history.

(56) References Cited

U.S. PATENT DOCUMENTS

| 5,883,074 | A | 3/1999 | Boggs et al. |
| 6,667,299 | B1 | 12/2003 | Ahlem et al. |
| 2003/0083231 | A1 | 5/2003 | Ahlem et al. |
| 2005/0256093 | A1 | 11/2005 | Duvold |
| 2007/0014719 | A1 | 1/2007 | Reading et al. |
| 2008/0004250 | A1 | 1/2008 | Lardy et al. |
| 2008/0021006 | A1 | 1/2008 | Lardy et al. |
| 2008/0058301 | A1 | 3/2008 | Lardy et al. |
| 2008/0070881 | A1 | 3/2008 | Lardy et al. |

FOREIGN PATENT DOCUMENTS

| WO | WO 91/00732 | 1/1991 |
| WO | WO 91/00733 | 1/1991 |
| WO | WO 01/23405 | 4/2001 |
| WO | WO 03/087121 | 10/2003 |
| WO | WO 2004/089304 | 10/2004 |

OTHER PUBLICATIONS

Schubert, et al, Stereospecific hydrogenation od 4-, 1,4-,4,6- and 1,4,6-3-ketosteroids by Clostridium Paraputrificum *Steroids Suppl 1*, 175-184, 1965.

*Primary Examiner*—Barbara P Badio
(74) *Attorney, Agent, or Firm*—Daryl Muenchau

(57) ABSTRACT

The instant invention provides potent antiandrogen compounds, such as 3β-acetoxyandrost-1,5-diene-17-ethylene ketal and 3β-hydroxyandrost-1,5-diene-17-ethylene ketal, and methods for their use in the prevention and treatment of biological conditions mediated by androgen receptors. Thus, for example, compounds of the invention are useful in the prevention and treatment of prostate cancer. Furthermore, it has been discovered that compounds of the invention are useful in the prevention and treatment of androgen-independent cancers such as androgen-independent prostate cancer. Finally, inventive compounds may be used to treat antiandrogen induced withdrawal syndrome.

4 Claims, No Drawings

PROSTATE CANCER TREATMENT

CROSS-REFERENCE TO RELATED APPLICATIONS

This application is a divisional application of U.S. application ser. No. 10/814,503, filed Mar. 30, 2004, now abandoned, which claims priority from U.S. provisional application No. 60/459,450, filed on Apr. 1, 2003, both of which are incorporated herein by reference.

FIELD OF THE INVENTION

The present invention relates to low molecular weight compounds, useful as antiandrogens, and in particular as antiandrogens with low androgenic activity. The invention further relates to methods for inhibiting androgen receptors and in treating androgen receptor-mediated conditions, such as prostate cancer, with compounds and compositions provided herein.

BACKGROUND OF THE INVENTION

Androgens play a major role in promoting the development and progression of prostate cancer. Consequently, since the first observation by Huggins and Hodges in 1941 (Cancer Res., 1941, 1:293-297), endocrine therapy remains the critical therapeutic option for advanced forms of prostate cancer. This therapy consists of androgen ablation by medical or surgical castration and/or inhibiting the receptor level action of androgens from both the testes and adrenal glands by antiandrogens. Thus, antiandrogens are generally used in conjunction with castration as combined androgen blockade (CAB). Unfortunately, after a brief clinical response to the hormonal therapy in most patients, the majority eventually develop symptomatic recurrences, which have been termed androgen-independent or hormone-refractory prostate cancer, within a few years. Indeed, in males prostate cancer is the most common malignancy and is the second leading cause of cancer-related death.

Antiandrogens include a number of compounds that are able to compete with androgens, such as dihydrotestosterone (DHT), an active metabolite of testosterone in the prostate, for the binding to the androgen receptor (AR). There are three non-steroidal antiandrogens available in the United States: flutamide, bicalutamide (casodex), and nilutamide. Monotherapy using these antiandrogens does not decrease androgen concentrations, offering potential quality-of-life benefits over castration-based approaches. However, specific side effects may be associated with such monotherapy, including gynecomastia and breast pain, hepatotoxicity, visual and respiratory disturbances, and alcohol intolerance (Kolvenbag, et al., Urology, 2001, 58(Suppl 2A): 16-23.).

In addition, antiandrogens have been reported to raise the amount of prostate-specific antigen (PSA), a tumor marker of prostate cancer and also an AR responsive gene, during hormonal therapy. In these cases, when antiandrogen therapy is terminated, PSA actually declines to 50% or less of its original value prior to therapy; this phenomenon is known as antiandrogen withdrawal syndrome. Thus, such patients benefit from the withdrawal of the majority of antiandrogens clinically used, including the above three drugs, as well as some steroid hormones, such as diethlystilbesterol and magestrol. The mechanisms responsible for antiandrogen withdrawal syndrome are not completely understood, although it is likely that AR gene mutations and/or AR coregulators, such as ARA70, are involved in the change of antiandrogens from antagonists to agonists. The remaining patients, not subject to antiandrogen withdrawal syndrome may be considered to have androgen-independent prostate cancer.

Thus, a need in the art exists for new and more effective antiandrogenic compounds with lower androgenic activities. In particular, there is a need for antiandrogenic compounds effective against prostate cancer and especially against androgen-independent prostate cancer.

Methods to analyze or characterize the effects of androgen receptor modulators, i.e., agonists and antagonists, have been described, e.g., Yeh, S., et al. (1997) Lancet 349, 852-853; Miyamoto, H., et al. (1998) Proc. Natl. Acad. Sci. USA 95, 7379-7384; Miyamoto, H., et al. (1998) Proc. Natl. Acad. Sci. USA 95, 11083-11088; Chang, H.-C., et al. (1999) Proc. Natl. Acad. Sci. USA 96, 11173-11177; Miyamoto, H., et al. (2003) Proc. Natl. Acad. Sci. USA 100, 4440-4444; Rahman, M. M., et al. (2003) Proc. Natl. Acad. Sci. USA 100, 5124-5129; Yeh, S. & Chang, C. (1996) Proc. Natl. Acad. Sci. USA 93, 5517-5521.

SUMMARY OF THE INVENTION

The instant invention provides potent antiandrogen compounds and methods for their use in the prevention and treatment of biological conditions mediated by androgen receptors. Thus, for example, compounds of the invention are useful in the prevention and treatment of prostate cancer. Furthermore, it has been discovered that compounds of the invention are useful in the prevention and treatment of androgen-independent cancers such as androgen-independent prostrate cancer. Finally, inventive compounds may be used to treat antiandrogen induced withdrawal syndrome.

Thus, there has been provided, in accordance with one aspect of the invention, compounds of structure I, prodrugs thereof, pharmaceutically acceptable salts thereof, stereoisomers thereof, tautomers thereof, and solvates thereof.

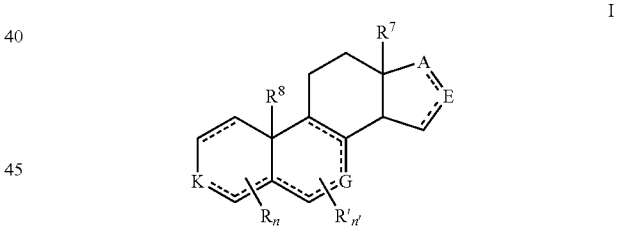

I

In compounds having structure I
A is —C(O)—, =$CR^9$—, or —$CR^9R^{10}$—;
E is —C(O)—, =$CR^5$—, or —$CR^5R^6$—, wherein A and E are not both —C(O);
G is —C(O)—, =$CR^3$—, or —$CR^3R^4$—;
K is —C(O)—, =$CR^1$—, or —$CR^1R^2$—;
$R^1$ is selected from the group consisting of —$OR^{11}$, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—$R^{12}$, —C(O)—$NR^{12}R^{13}$, —C(O)—$OR^{12}$, —C(S)—$R^{12}$, —C(S)—$OR^{12}$—$NR^{12}R^{13}$, —$NR^{12}$—C(O)—$R^{13}$, —$NR^{12}$—C(O)—$OR^{13}$, —$NR^{12}$—C(O)—$NR^{12}R^{13}$, and —$S(O)_{0-2}$—$R^{12}$;
$R^2$ is selected from the group consisting of —H, substituted and unsubstituted lower alkyl, substituted and unsubstituted lower alkene, and substituted and unsubstituted lower alkyne;

$R^3$ and $R^5$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

$R^4$ and $R^6$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

$R^7$ and $R^8$ are independently selected from the group consisting of —H and substituted and unsubstituted lower alkyl group;

$R^9$ and $R^{10}$ are independently selected from the group consisting of substituted and unsubstituted lower alkyl, substituted and unsubstituted lower alkene, substituted and unsubstituted lower alkyne, —OH, wherein $R^9$ and $R^{10}$ are not both —OH, substituted and unsubstituted lower alkoxy, and substituted and unsubstituted —S(O)$_{0-2}$ (lower alkyl), or $R^9$ and $R^{10}$, together with the carbon to which they are attached, form a 5-, 6-, or 7-membereterocyclyl or cycloalkyl group;

$R^{11}$ is selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —NR$^{12}$R$^{13}$, —S(O)$_2$—R$^{12}$, —S(O)$_2$—OR$^{12}$, or —P(O)(OR$^{12}$)(OR$^{13}$)$_{0-1}$;

$R^{12}$ and $R^{13}$ are, at each occurrence, independently selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, and substituted and unsubstituted heterocyclylalkyl;

$R^{14}$ and $R^{15}$ are, at each occurrence, independently selected from the group consisting of substituted and unsubstituted lower alkyl, substituted and unsubstituted lower alkene, substituted and unsubstituted lower alkyne, substituted and unsubstituted C$_{6-10}$ aryl, and substituted and unsubstituted C$_{7-12}$ arylalkyl;

R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

n and n' are independently 0, 1, or 2; and wherein the dashed lines in structure I represent carbon-carbon double bonds or carbon-carbon single bonds contained within the fused four-ring system, such that the compound comprises a 1,6-diene, 1,7-diene, 1,8-diene, 1,15-diene, 1,16-diene, 4,8-diene, 3,16-diene, 1,3,5-triene, 1,3,16-triene, 1,5,7-triene, 1,5,15-triene, 1,8,15-triene, 1,5,16-triene, or 1,5,7,15-tetraene, within the fused four-ring system.

In another aspect of the invention, there are provided compounds of structure II, prodrugs thereof, pharmaceutically acceptable salts thereof, stereoisomers thereof, tautomers thereof, or solvates thereof.

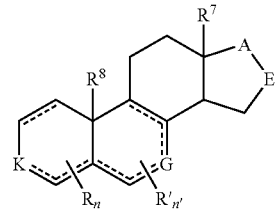

II

In compounds of structure II,

A is —C(O)— or —CR$^9$R$^{10}$—;

E is —C(O)— or —CR$^5$R$^6$—, wherein A and E are not both —C(O)—;

G is —C(O)—, =CR$^3$—, or —CR$^3$R$^4$—;

K is =C(OR$^{11}$)—, or —C(OR$^{11}$)R$^2$—;

$R^2$ is selected from the group consisting of —H, substituted and unsubstituted lower alkyl, substituted and unsubstituted lower alkene, and substituted and unsubstituted lower alkyne;

$R^3$ and $R^5$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

$R^4$ and $R^6$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

$R^7$ and $R^8$ are independently selected from the group consisting of —H and substituted and unsubstituted lower alkyl group;

$R^9$ and $R^{10}$ are independently selected from the group consisting of substituted and unsubstituted lower alkyl, substituted and unsubstituted lower alkene, substituted and unsubstituted lower alkyne, —OH, wherein $R^9$ and $R^{10}$ are not both —OH, substituted and unsubstituted lower alkoxy, and substituted and unsubstituted —S(O)$_{0-2}$ (lower alkyl), or $R^9$ and $R^{10}$, together with the carbon to which they are attached, form a 5-, 6-, or 7-member heterocyclyl or cycloalkyl group;

$R^{11}$ is selected from the group consisting of substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —NR$^{12}$R$^{13}$, —S(O)$_2$—R$^{12}$, —S(O)$_2$—OR$^{12}$, or —P(O)(OR$^{12}$)(OR$^{13}$)$_{0-1}$;

$R^{12}$ and $R^{13}$ are, at each occurrence, independently selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, and substituted and unsubstituted heterocyclylalkyl;

$R^{14}$ and $R^{15}$ are, at each occurrence, independently selected from the group consisting of substituted and unsubstituted lower alkyl, substituted and unsubstituted lower alkene, substituted and unsubstituted lower alkyne, substituted and unsubstituted $C_{6-10}$ aryl, and substituted and unsubstituted $C_{7-12}$ arylalkyl;

R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

n and n' are independently 0, 1, or 2; and wherein the dashed lines in structure II represent carbon-carbon double bonds or carbon-carbon single bonds contained within the fused four-ring system, such that the compound comprises a 1,3-diene, 1,5-diene, or 1,4,6-triene within the fused four-ring system.

In still another aspect of the invention, there are provided methods of treating or preventing a condition mediated by an androgen receptor comprising administering to a subject in need thereof, an effective amount of a compound having the structure III, prodrugs thereof, pharmaceutically acceptable salts thereof, stereoisomers thereof, tautomers thereof, or solvates thereof.

III

In compounds of structure III

A is —C(O)—, =CR$^9$—, or —CR$^9$R$^{10}$—;

E is —C(O)—, =CR$^5$—, or —CR$^5$R$^6$—, wherein A and E are not both —C(O);

G is —C(O)—, =CR$^3$—, or —CR$^3$R$^4$—;

K is —C(O)—, =CR$^1$—, or —CR$^1$R$^2$—;

R$^1$ is selected from the group consisting of —OR$^{11}$, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —O—C(O)—R$^{12}$, —C(O)—R$^{12}$, —C(O)—NR$^{12}$R$^{13}$, —C(O)—OR$^{12}$, —C(S)—R$^{12}$, —C(S)—OR$^{12}$, —NR$^{12}$R$^{13}$, —NR$^{12}$—C(O)—R$^{13}$, —NR$^{12}$—C(O)—OR$^{13}$, —NR$^{12}$—C(O)—NR$^{12}$R$^{13}$, and —S(O)$_{0-2}$—R$^{12}$;

R$^2$ is selected from the group consisting of —H, substituted and unsubstituted lower alkyl, substituted and unsubstituted lower alkene, and substituted and unsubstituted lower alkyne;

R$^3$ and R$^5$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

R$^4$ and R$^6$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

R$^7$ and R$^8$ are independently selected from the group consisting of —H and substituted and unsubstituted lower alkyl group;

R$^9$ and R$^{10}$ are independently selected from the group consisting of substituted and unsubstituted lower alkyl, substituted and unsubstituted lower alkene, substituted and unsubstituted lower alkyne, —OH, wherein R$^9$ and R$^{10}$ are not both —OH, substituted and unsubstituted lower alkoxy, and substituted and unsubstituted —S(O)$_{0-2}$ (lower alkyl), or R$^9$ and R$^{10}$, together with the carbon to which they are attached, form a 5-, 6-, or 7-member heterocyclyl or cycloalkyl group;

R$^{11}$ is selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —NR$^{12}$R$^{13}$, —S(O)$_2$—R$^{12}$, —S(O)$_2$—OR$^{12}$, or —P(O)(OR$^{12}$)(OR$^{13}$)$_{0-1}$;

R$^{12}$ and R$^{13}$ are, at each occurrence, independently selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, and substituted and unsubstituted heterocyclylalkyl;

R$^{14}$ and R$^{15}$ are, at each occurrence, independently selected from the group consisting of substituted and unsubstituted lower alkyl, substituted and unsubstituted lower alkene, substituted and unsubstituted lower alkyne, substituted and unsubstituted $C_{6-10}$ aryl, and substituted and unsubstituted $C_{7-12}$ arylalkyl;

R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$;

n and n' are independently 0, 1, or 2; and wherein the dashed lines in structure III represent carbon-carbon double bonds or carbon-carbon single bonds contained within the fused four-ring system, such that the compound comprises a 1,3-diene, 1,5-diene, 1,6-diene, 1,7-diene, 1,8-diene, 1,15-diene, 1,16-diene, 3,16-diene, 4,8-diene, 1,3,5-triene, 1,4,6-triene, 1,3,16-triene, 1,5,7-triene, 1,5,15-triene, 1,8,15-triene, 1,5,16-triene, or 1,5,7,15-tetraene, within the fused four-ring system.

In some embodiments of methods of treating or preventing a condition mediated by an androgen receptor, the condition is prostate cancer, and in particular, prostate cancer at an androgen-independent stage. In other embodiments, the condition is antiandrogen induced withdrawal syndrome, and the subject may be afflicted with prostate cancer.

In other embodiments of methods of treating or preventing a condition mediated by an androgen receptor, the compound comprises a 1,5-diene within the fused four-ring system. In other such embodiments, K is —CR$^1$R$^2$—, R$^1$ is —OR$^{11}$, or R$^{11}$ is —H, substituted or unsubstituted alkyl, —C(O)—R$^{12}$, —C(O)—NR$^{12}$R$^{13}$, or —C(O)—OR$^{12}$. In further embodiments, the compound comprises a 1,5-diene within the fused four-ring system, and R$^{11}$ is —H, or —C(O)—R$^{12}$.

The present invention also provides methods of inhibiting androgen receptors in vitro or in vivo comprising contacting an androgen receptor with an effective amount of a compound having the structure III, as described above. In some embodiments of such methods, the transactivation of androgen receptor is suppressed. In other embodiments, the androgen receptor is mutant or native androgen receptor.

In still other embodiments of methods of inhibiting androgen receptors in vitro or in vivo, the compound comprises a 1,5-diene within the fused four-ring system. In other such embodiments, K is —$CR^1R^2$—, $R^1$ is —$OR^{11}$, or $R^{11}$ is —H, substituted or unsubstituted alkyl, —C(O)—$R^{12}$, —C(O)—$NR^{12}R^{13}$, or —C(O)—$OR^{12}$. In further embodiments, the compound comprises a 1,5-diene within the fused four-ring system, and $R^{11}$ is —H, or —C(O)—$R^{12}$.

DETAILED DESCRIPTION OF THE INVENTION

The following abbreviations and terms are defined as follows: ADEK is 3β-acetoxy-17,17-ethylenedioxyandrost-1,5-diene-17-one (3β-acetoxyandrost-1,5-diene-17-ethylene ketal), adiol is Δ$^5$-androstenediol (3β,17β-dihydroxyandrost-5-ene), AR is androgen receptor, DHEA is dehydroepiandrosterone, DHT is dihydrotestosterone, ER is estrogen receptor, EtOH is ethanol, HF is hydroxyflutamide, Luc is luciferase, MMTV is mouse mammary tumor virus, PR is progesterone receptor, PSA is prostate specific antigen, R1881 is the synthetic androgen methyltrienolone (17α-methyl-17β-hydroxyestra-4,9(10),11-trien-3-one) and RBA is relative binding affinity.

Generally, reference to a certain element such as hydrogen or —H is meant to include all isotopes of that element. For example, if an R group is defined to include hydrogen or —H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl, norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms, and more preferred such groups have from 1 to 10 carbon atoms. Even more preferred such groups, also known as unsubstituted lower alkyl groups, have from 1 to 5 carbon atoms. Most preferred unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; and oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH=C(H)(CH$_3$), —CH=C(CH$_3$)$_2$, —C(CH$_3$)=C(H)$_2$, —C(CH$_3$)=C(H)(CH$_3$), —C(CH$_2$CH$_3$)=CH$_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus the phrase includes, but is not limited to, groups such as benzyl, diphenylmethyl, and 1-phenylethyl (—CH(C$_6$H$_5$)(CH$_3$)) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH$_2$C(=O)(C$_6$H$_5$), and —CH$_2$(2-methylphenyl) among others.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one or more of the ring members is bonded to a non-hydrogen atom such as described above with respect to substituted alkyl groups and substituted aryl groups. Examples include, but are not limited to, 2-methylbenzimidazolyl, 5-methylbenzimidazolyl, 5-chlorobenzthiazolyl, 1-methyl piperazinyl, 2-phenoxy-thiophene, and 2-chloropyridinyl among others. In addition, substituted heterocyclyl groups also include heterocyclyl groups in which the bond to the non-hyrogen atom is a bond to a carbon atom that is part of a substituted and unsubstituted aryl, substituted and unsubstituted arylalkyl, or unsubstituted heterocyclyl group. Examples include but are not limited to 1-benzylpiperidinyl, 3-phenylhiomorpholinyl, 3-(pyrrolidin-1-yl)-pyrrolidinyl, and 4-(piperidin-1-yl)-piperidinyl.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—CH₃) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted arylalkyl group. Examples include but are not limited to phenyl-(piperidin-1-yl)-methyl and phenyl-(morpholin-4-yl)-methyl.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, ethanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Prodrugs, as used in the context of the instant invention, includes those derivatives of the instant compounds which undergo in vivo metabolic biotransformation, by enzymatic or nonenzymatic processes, such as hydrolysis, to form a compound of the invention. Typical prodrugs include ester and ether moieties. Prodrugs can be employed to improve pharmaceutical or biological properties, as for example solubility, melting point, stability and related physicochemical properties, absorption, pharmacodynamics and other delivery-related properties.

In accordance with I.U.P.A.C. nomenclature, the carbon atoms of the fused four-ring system of the present invention are numbered as follows:

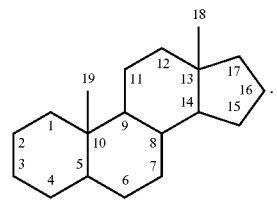

Tautomers refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, ketones are typically in equilibrium with their enol forms. Thus, ketones and their enols are referred to as tautomers of each other. As readily understood by one skilled in the art, a wide variety of functional groups and other structures may exhibit tautomerism, and all tautomers of compounds having structures I, II, or III are within the scope of the present invention.

Compounds of the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

In accordance with one aspect of the invention, there are provided compounds of structure I, prodrugs thereof, pharmaceutically acceptable salts thereof, stereoisomers thereof, tautomers thereof, and solvates thereof.

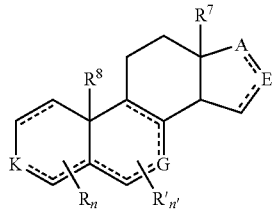

In compounds of structure I, A is —C(O)—, =CR$^9$—, or —CR$^9$R$^{10}$—; E is —C(O)—, =CR$^5$—, or —CR$^5$R$^6$—, wherein A and E are not both —C(O)—; G is —C(O)—, =CR$^3$—, or —CR$^3$R$^4$—and K is —C(O)—, =CR$^1$—, or —CR$^1$R$^2$—.

In certain embodiments of compounds having the structure I, A is —CR$^9$R$^{10}$—, E is —CR$^5$R$^6$—, G is —CR$^3$R$^4$—, or K is —C(OR$^{11}$)R$^2$—. In other such embodiments, A is —CR$^9$R$^{10}$— and K is —CR$^1$R$^2$—. In further embodiments, E is —CR$^5$R$^6$—, G is —CR$^3$R$^4$—, and K is —CR$^1$R$^2$—. In still further embodiments, A is —CR$^9$R$^{10}$—, E is —CR$^5$R$^6$—, G is —CR$^3$R$^4$—, and K is —CR$^1$R$^2$—. In other embodiments, A is —C(O)—, E is —C(O)—, G is —C(O)—, or K is —C(O)—.

The present invention also contemplates compounds of structure I having double bonds at particular positions as set forth below. Thus, in some embodiments, A is =CR$^9$—, G is =CR$^3$—, or E is =CR$^5$—. In other embodiments A is =CR$^9$— and E is =CR$^5$—.

In compounds of structure I, R$^1$ is selected from the group consisting of —OR$^{11}$, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —C(S)—OR$^{12}$, —NR$^{12}$R$^{13}$, —NR$^{12}$—C(O)—R$^{13}$, —NR$^{12}$—C(O)—OR$^{13}$, —NR$^{12}$—C(O)—NR$^{12}$R$^{13}$, and —S(O)$_{0-2}$—R$^{12}$. In some embodiments, R$^1$ is selected from the group consisting of —OR$^{11}$, substituted and unsubstituted alkyl, —C(O)—R$^{12}$, —C(O)—NR$^{12}$R$^{13}$, —C(O)—OR$^{12}$, —C(S)—R$^{12}$, —C(S)—OR$^{12}$, —NR$^{12}$R$^{13}$, —NR$^{12}$—C(O)—R$^{13}$, —NR$^{12}$—C(O)—OR$^{13}$, —NR$^{12}$—C(O)—NR$^{12}$R$^{13}$, and —S(O)$_{0-2}$—R$^{12}$. In other embodiments, R$^1$ is selected from the group consisting of —OR$^{11}$, substituted and unsubstituted alkyl, —NR$^{12}$R$^{13}$, —NR$^{12}$—C(O)—R$^{13}$, and —NR$^{12}$—C(O)—OR$^{13}$. In yet other embodiments, R$^1$ is —OR$^{11}$.

In compounds of structure I, R$^2$ is selected from the group consisting of —H, substituted and unsubstituted lower alkyl, substituted and unsubstituted lower alkene, and substituted and unsubstituted lower alkyne. In other embodiments, R$^2$ is —H.

In compounds of structure I, R$^3$ and R$^5$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$. In some embodiments, R$^3$ and R$^5$ are independently selected from the group consisting of —H, substituted and unsubstituted lower alkyl, substituted and unsubstituted lower alkyne, —CN, —COOR$^{14}$, —C(O)NR$^{14}$R$^{15}$, —NR$^{14}$R$^{15}$, —NR$^{14}$—C(O)—R$^{15}$, —OH, and substituted and unsubstituted lower alkoxy. In other embodiments, R$^3$ and R$^5$ are independently selected from the group consisting of —H, substituted and unsubstituted lower alkyl, substituted and unsubstituted lower alkyne, —OH, and substituted and unsubstituted lower alkoxy. In still other embodiments, R$^3$ or R$^5$ is —H, or both are —H.

In compounds of structure I, R$^4$ and R$^6$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$.

In compounds of structure I, R$^7$ and R$^8$ are independently selected from the group consisting of —H and substituted and unsubstituted lower alkyl. In some such embodiments, R$^7$ and R$^8$ are independently selected from unsubstituted lower alkyl. In other embodiments, R$^7$ or R$^8$ is methyl, or both are methyl.

In compounds of structure I, R$^9$ and R$^{10}$ are independently selected from the group consisting of substituted and unsubstituted lower alkyl, substituted and unsubstituted lower alkene, substituted and unsubstituted lower alkyne, —OH, wherein R$^9$ and R$^{10}$ are not both —OH, substituted and unsubstituted lower alkoxy, and substituted and unsubstituted —S(O)$_{0-2}$(lower alkyl), or R$^9$ and R$^{10}$, together with the carbon to which they are attached, form a 5-, 6-, or 7-member heterocyclyl or cycloalkyl group. In some embodiments R$^9$ is a —OH or substituted alkoxy, such as an acetyl and the like.

In other embodiments of compounds having structure I, R$^9$ and R$^{10}$, together with the carbon to which they are attached, form a 5-, 6-, or 7-member heterocyclyl or cycloalkyl group. Certain such embodiments, have the structure

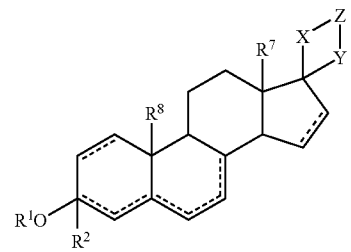

wherein,

X and Y are independently selected from the group consisting of —NR$^{14}$—, —O—, —S—, and substituted and unsubstituted C$_1$ alkyl;

Z is substituted or unsubstituted C$_{2-4}$ alkyl or substituted or unsubstituted —(CR$^{14}$R$^{15}$)$_{2-3}$—; and R$^2$ is as defined herein.

In other embodiments, R$^9$ and R$^{10}$, together with the carbon to which they are attached, form a 5-, 6-, or 7-member heterocyclyl. Typically the heterocycle is a 5- or 6-member heterocycle such as a ketal or thioketal In compounds of structure I, R$^{11}$ is selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —NR$^{12}$R$^{13}$, —S(O)$_2$—R$^{12}$, —S(O)$_2$—OR$^{12}$, and —P(O)(OR$^{12}$)(OR$^{13}$)$_{0-1}$. In some embodiments, R$^{11}$ is selected from the group consisting of substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —NR$^{12}$R$^{13}$, —S(O)$_2$—R$^{12}$, —S(O)$_2$—OR$^{12}$, or —P(O)(OR$^{12}$)(OR$^{13}$)$_{0-1}$. In other embodiments, R$^{11}$ is selected from the group consisting of —H, substituted and unsubstituted alkyl, —C(O)—R$^{12}$, —C(O)—NR$^{12}$R$^{13}$, and —C(O)—OR$^{12}$. In still other embodiments, R$^{11}$ is selected from the group consisting of —H, —C(O)—R$^{12}$ and —C(O)—OR$^{12}$. In some embodiments, R$^{11}$ is —C(O)—R$^{12}$.

In compounds of structure I, R$^{12}$ and R$^{13}$ are, at each occurrence, independently selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, and substituted and unsubstituted heterocyclylalkyl. In some embodiments, R$^{12}$ and R$^{13}$ are, at each occurrence, independently selected from the group consisting of —H, substituted and unsubstituted alkyl, substituted and unsubstituted alkene, and substituted and unsubstituted alkyne. In some such embodiments, R$^{12}$ is selected from the group consisting of —H and substituted and unsubstituted lower alkyl. In still other embodiments where R$^{11}$ is —C(O)—R$^{12}$, R$^{12}$ is unsubstituted lower alkyl. In some embodiments, R$^{13}$ is —H.

In compounds of structure I, R$^{14}$ and R$^{15}$ are, at each occurrence, independently selected from the group consisting of substituted and unsubstituted lower alkyl, substituted and unsubstituted lower alkene, substituted and unsubstituted lower alkyne, substituted and unsubstituted C$_{6-10}$ aryl, and substituted and unsubstituted C$_{7-12}$ arylalkyl.

In compounds of structure I, R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$. In other embodiments R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —OH, and substituted and unsubstituted lower alkoxy. In still other embodiments, R and R' are, at each occurrence, independently selected from the group consisting of —F and substituted and unsubstituted lower alkyl, —OH, and substituted and unsubstituted lower alkoxy.

In compounds of structure I, typically, n and n' are independently 0, 1, or 2. In some embodiments, n and n' are independently 1 or 2. In other embodiments, n and n' are independently 0 or 1. Thus, the A ring of the fused four-ring system of structure I may have one or two R substituents at position 1, one or two R substituents at position 2, and so forth. Alternatively, the A ring may have two R substituents at different positions such as position 2 and 4. Similarly, in some embodiments the B-ring may have one or two R' substituents at position 6 or a single R' at position 9, among other embodiments.

In compounds of structure I, the dashed lines in structure I represent carbon-carbon double bonds or carbon-carbon single bonds contained within the fused four-ring system, such that the compound comprises a 1,6-diene, 1,7-diene, 1,8-diene, 1,15-diene, 1,16-diene, 4,8-diene, 3,16-diene, 1,3, 5-triene, 1,3,16-triene, 1,5,7-triene, 1,5,15-triene, 1,8,15-triene, 1,5,16-triene, or 1,5,7,15-tetraene, within the fused four-ring system. The 1,8-diene includes both 1,8(9)- and 1,8(14)-dienes, while the 1,8,15-triene includes 1,8(9)- and 1,8(14)-trienes. In some embodiments, the compound comprises a 1,6-diene, 1,7-diene, 1,8-diene, 1,15-diene, 1,16-diene, 4,8-diene, or 3,16-diene, within the fused four-ring system. In other embodiments, the compound comprises a 1,3,5-triene, 1,3,16-triene, 1,5,7-triene, 1,5,15-triene, 1,8,15-triene, 1,5,16-triene, or 1,5,7,15-tetraene within the fused four-ring system.

In another aspect of the invention, there are provided compounds of structure II, prodrugs thereof, pharmaceutically acceptable salts thereof, stereoisomers thereof, tautomers thereof, or solvates thereof.

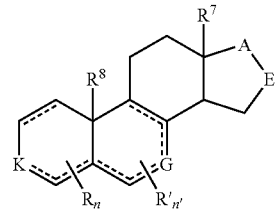

II

In compounds of structure II, A is —C(O)— or —CR$^9$R$^{10}$—; E is —C(O)— or —CR$^5$R$^6$—, wherein A and E are not both —C(O)—; G is —C(O)—, =CR$^3$—, or —CR$^3$R$^4$—; and K is =C(OR$^{11}$)—, or —C(OR$^{11}$)R$^2$—.

In certain embodiments of compounds having the structure II, A is —CR$^9$R$^{10}$—, E is —CR$^5$R$^6$—, G is —CR$^3$R$^4$—, or K is —C(OR$^{11}$)R$^2$—. In other such embodiments, A is —CR$^9$R$^{10}$—, and K is —C(OR$^{11}$)R$^2$—. In further embodiments, E is —CR$^5$R$^6$—, G is —CR$^3$R$^4$—, and K is —C(OR$^{11}$)R$^2$—. In still further embodiments, A is —CR$^9$R$^{10}$—, E is —CR$^5$R$^6$—, G is —CR$^3$R$^4$—, and K is —C(OR$^{11}$)R$^2$—. In other embodiments, A is —C(O)—, E is —C(O)—, or G is —C(O)—. Alternatively, G is =CR$^3$.

In compounds of structure II, R$^2$ is selected from the group consisting of —H, substituted and unsubstituted lower alkyl, substituted and unsubstituted lower alkene, and substituted and unsubstituted lower alkyne. In other embodiments, R$^2$ is —H.

In compounds of structure II, R$^3$ and R$^5$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$. In some embodiments, R$^3$ and R$^5$ are independently selected from the group consisting of —H, substituted and unsubstituted lower alkyl, substituted and unsubstituted lower alkyne, —CN, —COOR$^{14}$, —C(O)NR$^{14}$R$^{15}$, —NR$^{14}$R$^{15}$, —NR$^{14}$—C(O)—R$^{15}$, —OH, and substituted and unsubstituted lower alkoxy. In other embodiments, R$^3$ and R$^5$ are independently selected from the group consisting of —H, substituted and unsubstituted lower alkyl, substituted and unsubstituted lower alkyne, —OH, and substituted and unsubstituted lower alkoxy. In still other embodiments, R$^3$ or R$^5$ is —H, or both are —H.

In compounds of structure II, R$^4$ and R$^6$ are independently selected from the group consisting of —H, —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$.

In compounds of structure II, R$^7$ and R$^8$ are independently selected from the group consisting of —H and substituted and unsubstituted lower alkyl. In some such embodiments, R$^7$ and R$^8$ are independently selected from unsubstituted lower alkyl. In other embodiments, R$^7$ or R$^8$ is methyl, or both are methyl.

In compounds of structure II, R$^9$ and R$^{10}$ are independently selected from the group consisting of substituted and unsubstituted lower alkyl, substituted and unsubstituted lower alkene, substituted and unsubstituted lower alkyne, —OH, wherein R$^9$ and R$^{10}$ are not both —OH, substituted and unsubstituted lower alkoxy, and substituted and unsubstituted —S(O)$_{0-2}$(lower alkyl); or R$^9$ and R$^{10}$, together with the carbon to which they are attached, form a 5-, 6-, or 7-member heterocyclyl or cycloalkyl group. In some such embodiments, R$^9$ and R$^{10}$, together with the carbon to which they are attached, form a 5-, 6-, or 7-member heterocyclyl or cycloalkyl group. In some embodiments, R$^9$ and R$^{10}$, together with the carbon to which they are attached, form a 5-, 6-, or 7-member heterocyclyl. Typically the heterocycle is a 5- or 6-member heterocycle such as a ketal.

In compounds of structure II, R$^{11}$ is selected from the group consisting of substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—R$^{12}$, —C(O)—NR$^{12}$R$^{13}$, —C(O)—OR$^{12}$, —C(S)—R$^{12}$, —NR$^{12}$R$^{13}$, —S(O)$_2$—R$^{12}$, —S(O)$_2$—OR$^{12}$, and —P(O)(OR$^{12}$)(OR$^{13}$)$_{0-1}$. In some embodiments, R$^{11}$ is selected from the group consisting of substituted and unsubstituted alkyl, —C(O)—R$^{12}$, —C(O)—NR$^{12}$R$^{13}$, and —C(O)—OR$^{12}$. In other embodiments, R$^{11}$ is selected from the group consisting of —C(O)—R$^{12}$ and —C(O)—OR$^{12}$. In still other embodiments, R$^{11}$ is —C(O)—R$^{12}$.

In compounds of structure II, R$^{12}$ and R$^{13}$ are, at each occurrence, independently selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, and substituted and unsubstituted heterocyclylalkyl. In some embodiments, R$^{12}$ and R$^{13}$ are, at each occurrence, independently selected from the group consisting of —H, substituted and unsubstituted alkyl, substituted and unsubstituted alkene, and substituted and unsubstituted alkyne. In some such embodiments, R$^{12}$ is selected from the group consisting of —H and substituted and unsubstituted lower alkyl. In still other embodiments where R$^{11}$ is —C(O)—R$^{12}$, R$^{12}$ is unsubstituted lower alkyl. In some embodiments, R$^{13}$ is —H.

In compounds of structure II, R$^{14}$ and R$^{15}$ are, at each occurrence, independently selected from the group consisting of substituted and unsubstituted lower alkyl, substituted and unsubstituted lower alkene, substituted and unsubstituted lower alkyne, substituted and unsubstituted C$_{6-10}$ aryl, and substituted and unsubstituted C$_{7-12}$ arylalkyl.

In compounds of structure II, R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —CN, —COOR$^{14}$, —C(O)NR$^{14}$R$^{15}$, —NO$_2$, —NR$^{14}$R$^{15}$, —NR$^{14}$—C(O)—R$^{15}$, —OH, substituted and unsubstituted lower alkoxy, and —S(O)$_{0-2}$R$^{14}$. In other embodiments R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —OH, and substituted and unsubstituted lower alkoxy. In still other embodiments, R and R' are, at each occurrence, independently selected from the group consisting of —F and substituted and unsubstituted lower alkyl, —OH, and substituted and unsubstituted lower alkoxy.

In compounds of structure II, typically, n and n' are independently 0, 1, or 2. In some embodiments, n and n' are independently 1 or 2. In other embodiments, n and n' are independently 0 or 1. Thus, the A ring of the fused four-ring system of structure I may have one or two R substituents at position 1, one or two R substituents at position 2, and so forth. Alternatively, the A ring may have two R substituents at different positions such as position 2 and 4. Similarly, in some embodiments the B-ring may have one or two R' substituents at position 6 or a single R' at position 9, among other embodiments.

In compounds of structure II, the dashed lines in structure II represent carbon-carbon double bonds or carbon-carbon single bonds contained within the fused four-ring system, such that the compound comprises a 1,3-diene, 1,5-diene, or 1,4,6-triene within the fused four-ring system. In some embodiments, the compound comprises a 1,3-diene or 1,4,6-triene within the fused four-ring system. In other embodiments, the compound comprises a 1,5-diene within the fused four-ring system. Certain such embodiments have the structure IIA:

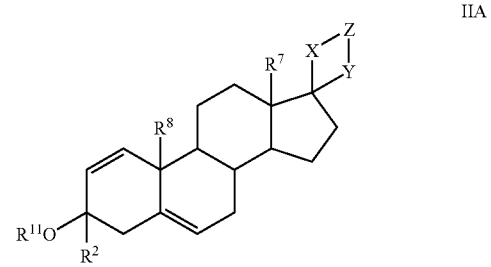

IIA wherein,

X and Y are independently selected from the group consisting of —NR$^{14}$—, —O—, —S—, and substituted and unsubstituted C$_1$ alkyl;

Z is substituted or unsubstituted C$_{2-4}$ alkyl, e.g., —CH$_2$—CH$_2$— or —CH$_2$—CH$_2$—CH$_2$—, or substituted or unsubstituted —(CR$^{14}$R$^{15}$)$_{2-3}$—; and R$^2$ is as previously defined.

Thus, the invention provides compounds having the structures:

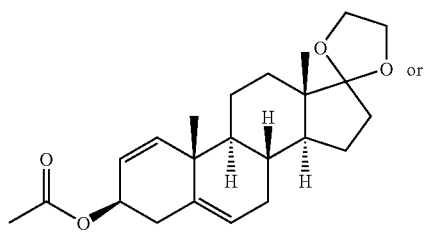

-continued

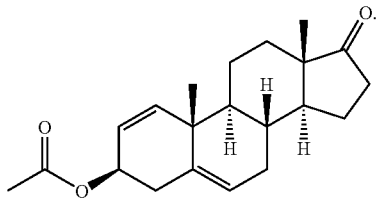

In still another aspect of the invention, there are provided methods of treating or preventing a condition mediated by an androgen receptor comprising administering to a subject in need thereof, an effective amount of a compound having the structure III, prodrugs thereof, pharmaceutically acceptable salts thereof, stereoisomers thereof, tautomers thereof, or solvates thereof.

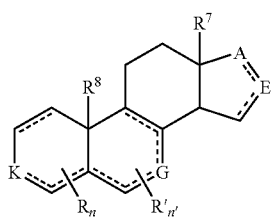

III

In compounds of structure III

A is —C(O)—, =$CR^9$—, or —$CR^9R^{10}$—;

E is —C(O)—, =$CR^5$—, or —$CR^5R^6$—, wherein A and E are not both —C(O);

G is —C(O)—, =$CR^3$—, or —$CR^3R^4$—;

K is —C(O)—, =$CR^1$—, or —$CR^1R^2$—;

$R^1$ is selected from the group consisting of —$OR^{11}$, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—$R^{12}$, —C(O)—$NR^{12}R^{13}$, —C(O)—$OR^{12}$, —C(S)—$R^{12}$, —C(S)—$OR^{12}$, —$NR^{12}R^{13}$, —$NR^{12}$—C(O)—$R^{13}$, —$NR^{12}$—C(O)—$OR^{13}$, —$NR^{12}$—C(O)—$NR^{12}R^{13}$, and —$S(O)_{0-2}$—$R^{12}$;

$R^2$ is selected from the group consisting of —H, substituted and unsubstituted lower alkyl, substituted and unsubstituted lower alkene, and substituted and unsubstituted lower alkyne;

$R^3$ and $R^5$ are independently selected from the group consisting of —H, —F, —Cl, —Br, —I, substituted and unsubstituted lower alkyl, substituted and unsubstituted lower alkene, substituted and unsubstituted lower alkyne, —CN, —$COOR^{14}$, —C(O)$NR^{14}R^{15}$, —$NO_2$, —$NR^{14}R^{15}$, —$NR^{14}$—C(O)—$R^{15}$, —OH, substituted and unsubstituted lower alkoxy, and —$S(O)_{0-2}R^{14}$;

$R^4$ and $R^6$ are independently selected from the group consisting of —H, —F, —Cl, —Br, —I, substituted and unsubstituted lower alkyl, substituted and unsubstituted lower alkene, substituted and unsubstituted lower alkyne, —CN, —$COOR^{14}$, —C(O)$NR^{14}R^{15}$, —$NO_2$, —$NR^{14}R^{15}$, —$NR^{14}$—C(O)—$R^{15}$, —OH, substituted and unsubstituted lower alkoxy, and —$S(O)_{0-2}R^{14}$;

$R^7$ and $R^8$ are independently selected from the group consisting of —H and substituted and unsubstituted lower alkyl group;

$R^9$ and $R^{10}$ are independently selected from the group consisting of substituted and unsubstituted lower alkyl, substituted and unsubstituted lower alkene, substituted and unsubstituted lower alkyne, —OH, wherein $R^9$ and $R^{10}$ are not both —OH, substituted and unsubstituted lower alkoxy, and substituted and unsubstituted —$S(O)_{0-2}$(lower alkyl), or $R^9$ and $R^{10}$, together with the carbon to which they are attached, form a 5-, 6-, or 7-member heterocyclyl or cycloalkyl group;

$R^{11}$ is selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, substituted and unsubstituted heterocyclylalkyl, —C(O)—$R^{12}$, —C(O)—$NR^{12}R^{13}$, —C(O)—$OR^{12}$, —C(S)—$R^{12}$, —$NR^{12}R^{13}$, —$S(O)_2$—$R^{12}$, —$S(O)_2$—$OR^{12}$, or —$P(O)(OR^{12})(OR^{13})_{0-1}$;

$R^{12}$ and $R^{13}$ are, at each occurrence, independently selected from the group consisting of —H, substituted and unsubstituted alkyl, substituted and unsubstituted alkene, substituted and unsubstituted alkyne, substituted and unsubstituted aryl, substituted and unsubstituted arylalkyl, substituted and unsubstituted heterocyclyl, and substituted and unsubstituted heterocyclylalkyl;

$R^{14}$ and $R^{15}$ are, at each occurrence, independently selected from the group consisting of substituted and unsubstituted lower alkyl, substituted and unsubstituted lower alkene, substituted and unsubstituted lower alkyne, substituted and unsubstituted $C_{6-10}$ aryl, and substituted and unsubstituted $C_{7-12}$ arylalkyl;

R and R' are, at each occurrence, independently selected from the group consisting of —F, —Cl, —Br, —I, substituted and unsubstituted lower alkyl, substituted and unsubstituted lower alkene, substituted and unsubstituted lower alkyne, —CN, —$COOR^{14}$, —C(O)$NR^{14}R^{15}$, —$NO_2$, —$NR^{14}R^{15}$, —$NR^{14}$—C(O)—$R^{15}$, —OH, substituted and unsubstituted lower alkoxy, and —$S(O)_{0-2}R^{14}$;

n and n' are independently 0, 1, or 2; and wherein the dashed lines in structure III represent carbon-carbon double bonds or carbon-carbon single bonds contained within the fused four-ring system, such that the compound comprises a 1,3-diene, 1,5-diene, 1,6-diene, 1,7-diene, 1,8-diene, 1,15-diene, 1,16-diene, 3,16-diene, 4,8-diene, 1,3,5-triene, 1,4,6-triene, 1,3,16-triene, 1,5,7-triene, 1,5,15-triene, 1,8,15-triene, 1,5,16-triene, or 1,5,7,15-tetraene, within the fused four-ring system.

In the compounds described herein, the hydrogen atoms at the 8, 9 and 14 positions respectively are typically in the β-, α- and α-configurations.

In some embodiments of methods of treating or preventing a condition mediated by an androgen receptor, the condition is prostate cancer, and in particular, prostate cancer at an androgen-independent stage. In other embodiments, the condition is antiandrogen induced withdrawal syndrome, and the subject may be afflicted with prostate cancer. In still further embodiments, the condition is benign prostatic hypertrophy, hirsutism, acne, androgenic alopecia, or ovulatory dysfunction in hyperandrogenic women, such as, for example, polycystic ovary syndrome patients. In some embodiments, the compounds disclosed herein are used to ameliorate and/or slow the progression of one or more of these conditions.

In other embodiments of methods of treating, preventing or slowing the progression of a condition mediated by an androgen receptor, the compound comprises a 1,5-diene within the fused four-ring system. In other such embodiments, K is —$CR^1R^2$—, $R^1$ is —$OR^{11}$, or $R^{11}$ is —H, substituted or unsubstituted alkyl, —C(O)—$R^{12}$, —C(O)—$NR^{12}R^{13}$, or —C(O)—$OR^{12}$. In further embodiments, the compound comprises a 1,5-diene within the fused four-ring system, and $R^{11}$ is —H, or —C(O)—$R^{12}$. Thus, the invention provides methods of treating, preventing or ameliorating a condition mediated by an androgen receptor using compounds disclosed herein. Such compounds include ADEK, 3β-hydroxyandrosta-1,5-dien-17,17-ethylene ketal, 3β-hydroxyandrosta-1,5-dien-17-one and 3β-acetoxyandrosta-1,5-dien-17-one.

While not wishing to be bound by any theory, it is believed that the compounds of the present invention are advantageously used in treating androgen-receptor mediated conditions because, among other things, they inhibit the activity of Adiol. The latter compound is unique among naturally occurring androgens in that its transactivation of the androgen receptor is not inhibited by previously known antiandrogens such as hydroxyflutamide or bicalutamide. Thus, Adiol activity can contribute to, e.g., androgen-independent prostate cancer. In contrast, as shown in Example 6, inventive compounds repress Adiol-induced AR transcription and would be expected to show efficacy against androgen-independent prostate cancer.

The present invention thus provides methods of inhibiting androgen receptors in vitro or in vivo comprising contacting an androgen receptor with an effective amount of a compound, e.g., a compound having the structure I, II or III. In some embodiments of such methods, the transactivation of androgen receptor is suppressed. In other embodiments, the androgen receptor is mutant or native androgen receptor. Such embodiments include methods to modulate the biological activity and/or the level of androgen receptor activity, e.g., in humans or mammals who have, or who are disposed to develop, an androgen receptor related condition or symptom. Such modulation can be effected in cells in vitro or in vivo. Compounds such as those described herein, or other androgen receptor modulators, e.g., as described in U.S. Pat. Nos. 6,645,974 B2, 6,569,896 B2, 6,696,459 B1 or 6,710,037 B2, can be characterized by their capacity to antagonize the activity of androgen receptor agonists such as adiol. The capacity of any selected test compound to modulate or antagonize androgen receptor activity or level in the presence or absence of an agonist such as adiol is optionally compared to the activity of a reference compound such as ADEK or another compound disclosed herein in the same or a suitable similar assay. Such information can then be used to characterize the test compound's capacity to antagonize the activity of androgen receptor agonists such as adiol. In these methods, test compounds can be assayed at two, three, four or more concentrations that range from about 0.01 nM to about 10 mM, e.g., at one or more of about 0.01 nM, 0.1 nM, 1.0 nM, 10 nM, 100 nM, 1 μM, 5 μM, 10 μM, 50 μM, 100 μM, 500 μM, 1 mM and 10 mM. Test compounds that are capable of antagonizing Adiol-stimulated AR activity can then be used to treat the conditions described herein.

Such assays can be performed essentially as described in the examples described herein, e.g., by contacting the test compound with a suitable AR assay system (under suitable conditions and for a sufficient time) in the presence and/or absence of an AR agonist such as Adiol. Any of these assays can optionally be performed in the presence or absence of other AR modulators such as DHT, testosterone, HF or casodex to characterize the effects of a test compound or a compound described herein to affect the activity of such AR modulators. Other indirect assays, e.g., measurement of PSA, can optionally also be used to characterize the compounds.

The present invention also provides methods of inhibiting androgen receptors in vitro or in vivo comprising contacting an androgen receptor with an effective amount of a compound having the structure III, as described above. In some embodiments of such methods, the transactivation of androgen receptor is suppressed. In other embodiments, the androgen receptor is mutant or native androgen receptor.

As is apparent from the foreging, the invention provides method of inhibiting an androgen receptor in vitro or in vivo comprising contacting the androgen receptor with an effective amount of a compound disclosed herein, e.g., a compound having the structure I, II or III, or a prodrug of the compound, a pharmaceutically acceptable salt of the compound, a stereoisomer of the compound, a tautomer of the compound, or a solvate of such compounds. In these methods, exemplary compounds of structure III, include compounds where the compound comprises a 1,3-diene, 1,5-diene, 1,6-diene, 1,7-diene, 1,8-diene, 1,15-diene, 1,16-diene, 3,16-diene, 4,8-diene, 1,3,5-triene, 1,4,6-triene, 1,3,16-triene, 1,5,7-triene, 1,5,15-triene, 1,8,15-triene, 1,5,16-triene, or 1,5,7,15-tetraene, within the fused four-ring system. In these methods, transactivation of androgen receptor can be detectably suppressed for mutant or native androgen receptors. In some of these embodiments, K is —$CR^1R^2$—, e.g., —CH(OH)—, —C(CH$_3$)(OH)—, —C(CH$_3$)(ester)- or —C(C≡CH)(OH)— where the hydroxyl or ester is in the α- or β-configuration.

In still other embodiments of methods of inhibiting androgen receptors in vitro or in vivo, the compound comprises a 1,5-diene within the fused four-ring system. In other such embodiments, K is —$CR^1R^2$—, $R^1$ is —$OR^{11}$, or $R^{11}$ is —H, substituted or unsubstituted alkyl, —C(O)—$R^{12}$, —C(O)—$NR^{12}R^{13}$, or —C(O)—$OR^{12}$. In further embodiments, the compound comprises a 1,5-diene within the fused four-ring system, and $R^{11}$ is —H, or —C(O)—$R^{12}$. Thus, for example, the present invention provides methods of inhibiting androgen receptors in vitro or in vivo, the compound having the structure

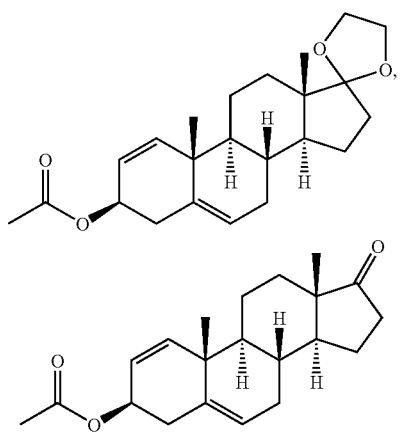

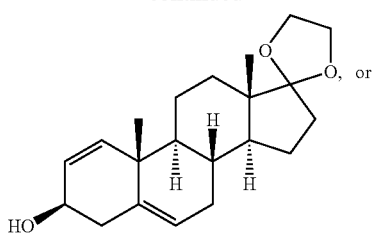

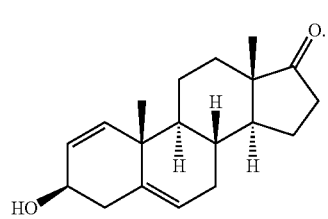

Compounds of structure I, II, or III may be synthesized from known starting materials as shown in Schemes 1-17 and the Examples. By way of example and not limitation, 1,5-dienes such as compounds 3-6, may be synthesized from the 1,4-diene, 1, using standard synthetic transformations. For example, protection of 1 as the 17-ethylene ketal, followed by isomerization of the 1,4-diene to the 1,5 diene under basic conditions gives 3. The latter compound may be further transformed to 5 by reduction and esterification. Compound 5 may be deprotected to give compounds 6 and 7, or may undergo carbonyl addition reactions to give compounds such as 8, as in Scheme 2. Scheme 3 illustrates the synthesis of 1,4-diene derivatives that may be used as starting materials for the synthesis of invention compounds. The remaining schemes show synthetic routes to various dienes, trienes, and tetraenes of the invention, and one skilled in the art will recognize that these routes may be readily modified to produce the desired compounds of the invention. In some cases, it will be convenient to use starting compounds that contain 1 or 2 R and/or R' moieties or where a variable group usch as E or G is substituted. In other cases, moieties are added to the steroid molecule at R R', E and/or G after synthesis.

Scheme 1: Synthesis of 1,5-dienes is outlined below.

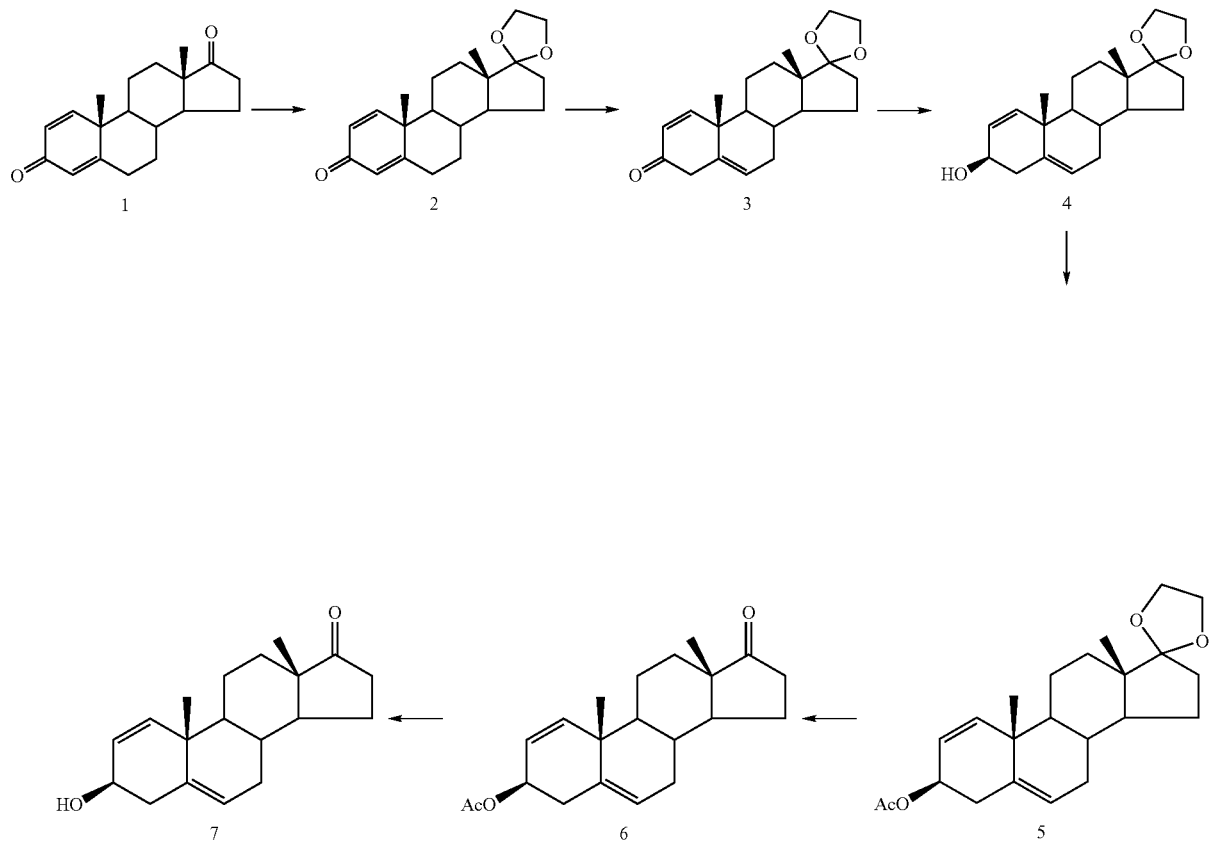

Scheme 2: Synthesis of 1,5-dienes is outlined below using an alternate route.
R = H, Alkyl, fluoroalkyl
-continued
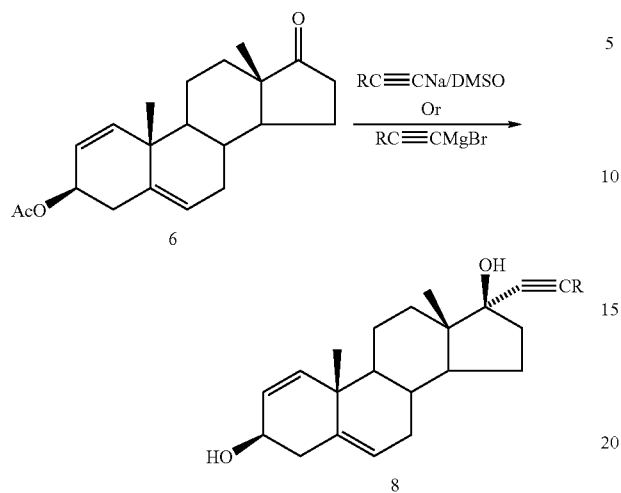
Scheme 3: Synthesis of 1,4-dienes is outlined below.
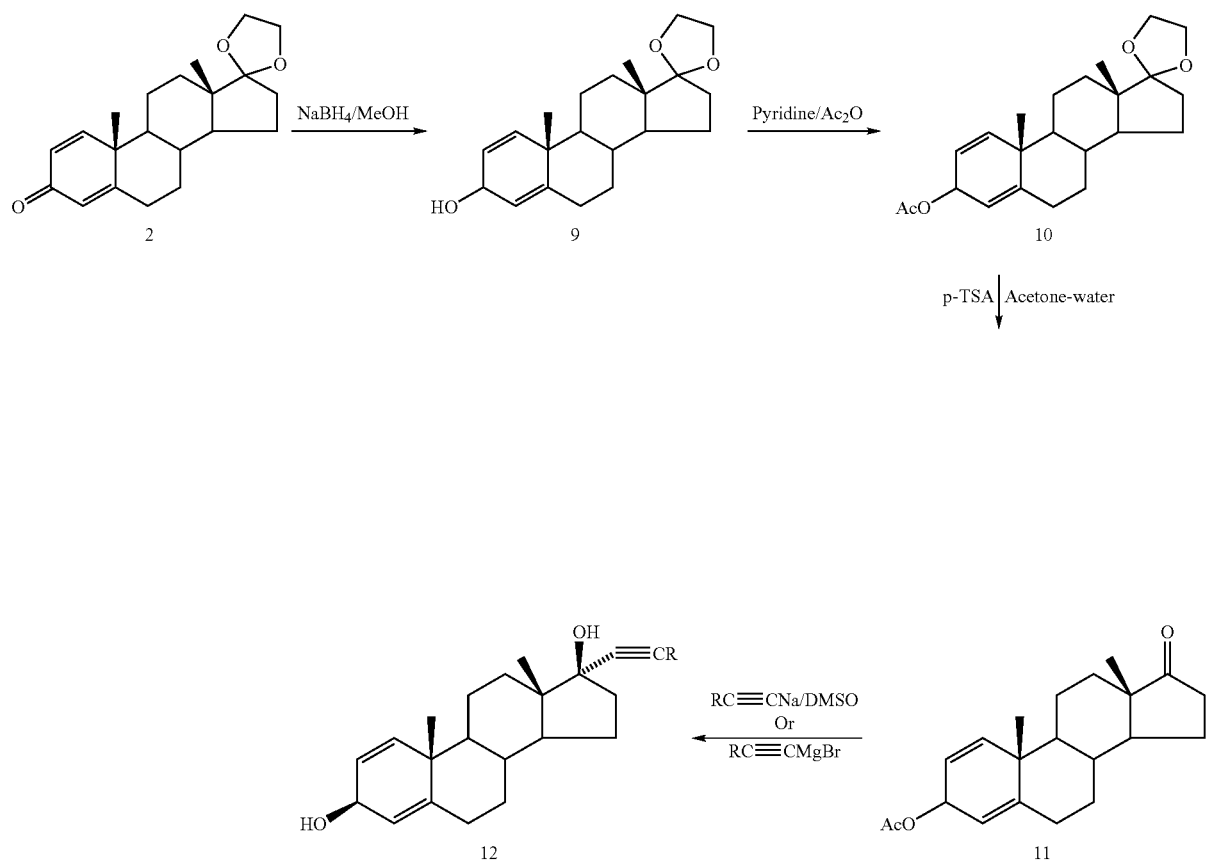
R = H, Alkyl, fluoroalkyl Scheme 4: Synthesis of 1-ene and 1,4-dienes is outlined below.
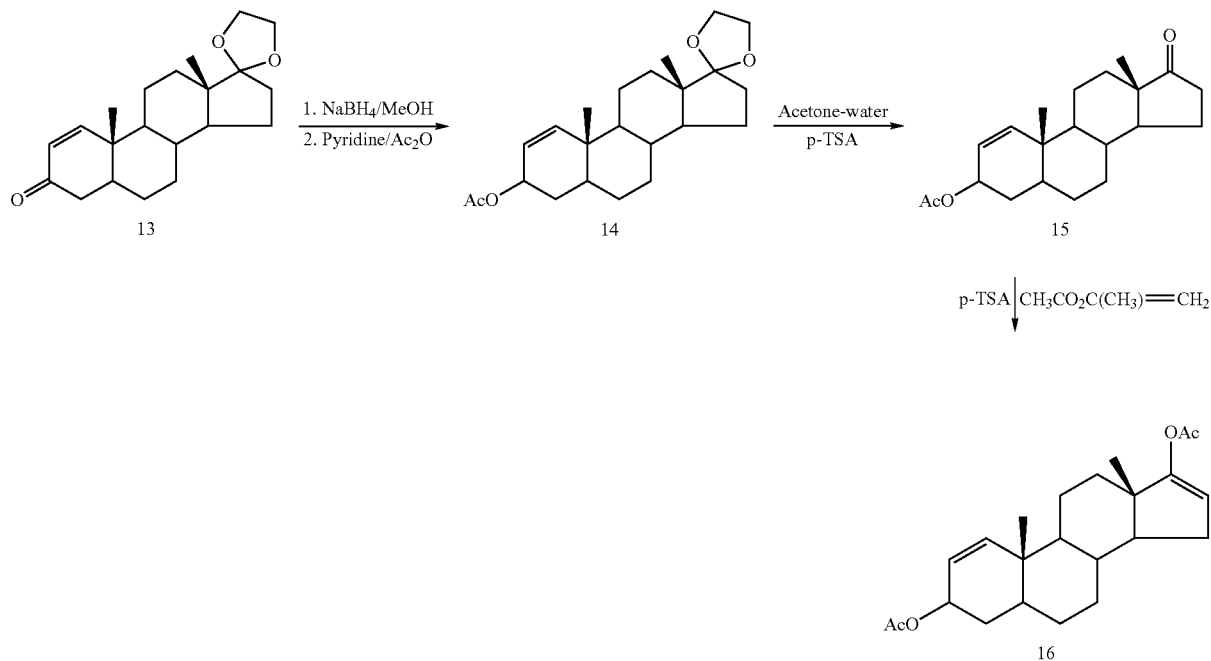
Scheme 5: Synthesis of 1,3-dienes is outlined below.
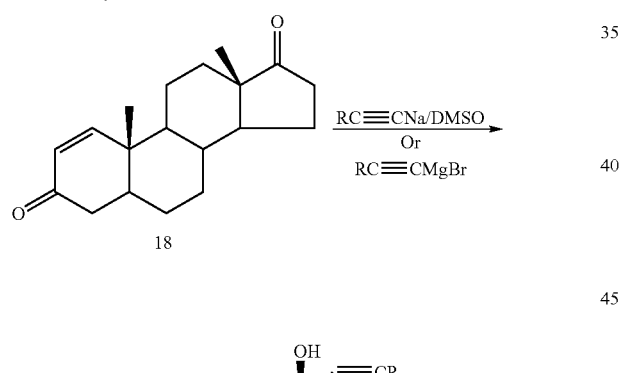
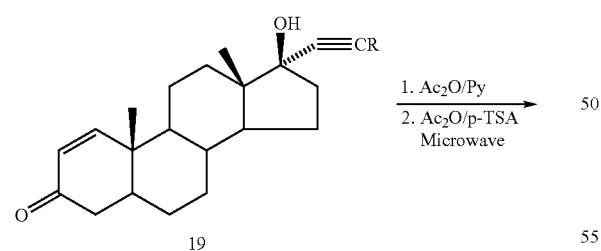
Scheme 6: Synthesis of 3,16-dienes is outlined below.
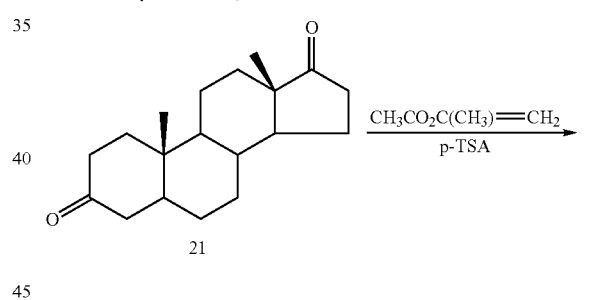
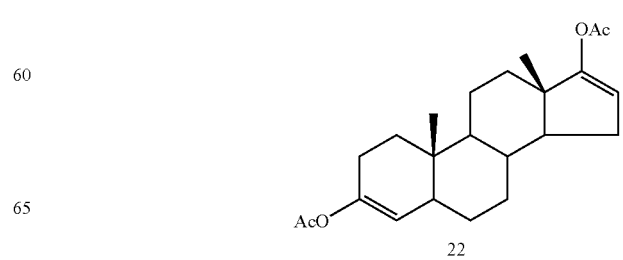

Scheme 7: Synthesis of 1,6-dienes and 1,7-dienes is outlined below.
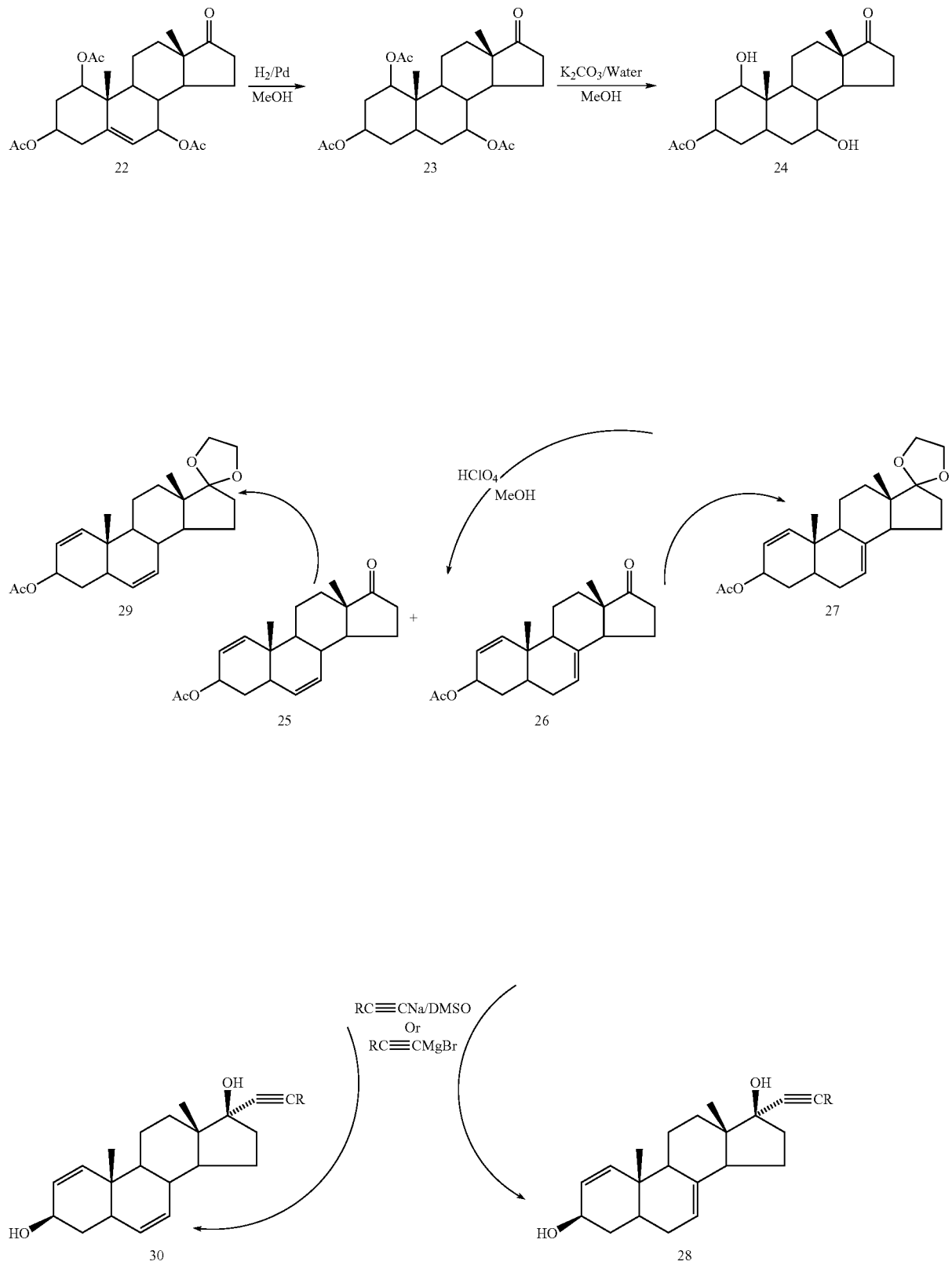
R = H, Alkyl, fluoroalkyl Scheme 8: Synthesis of 1,15-dienes is outlined below.
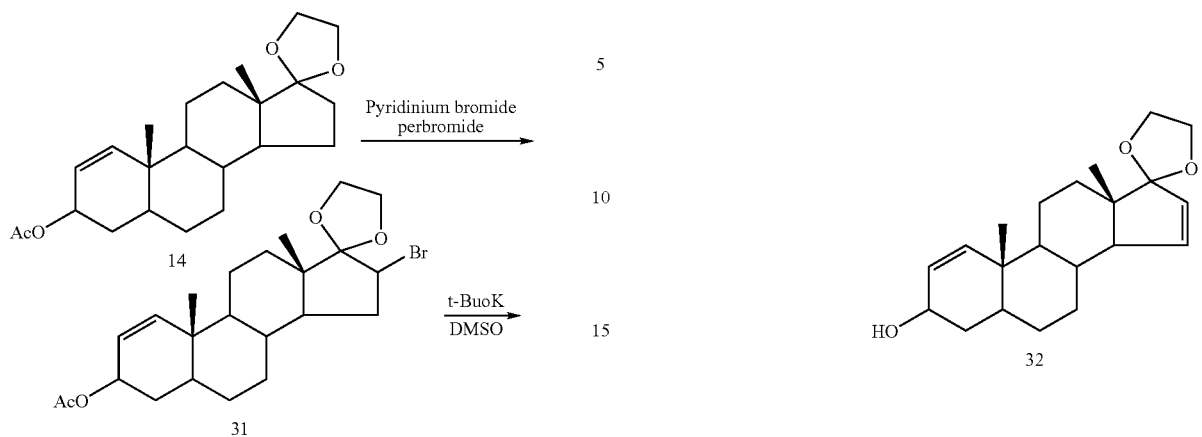
Scheme 9: Synthesis of 1,8(9)-dienes and 1,8(14)-dienes is outlined below.
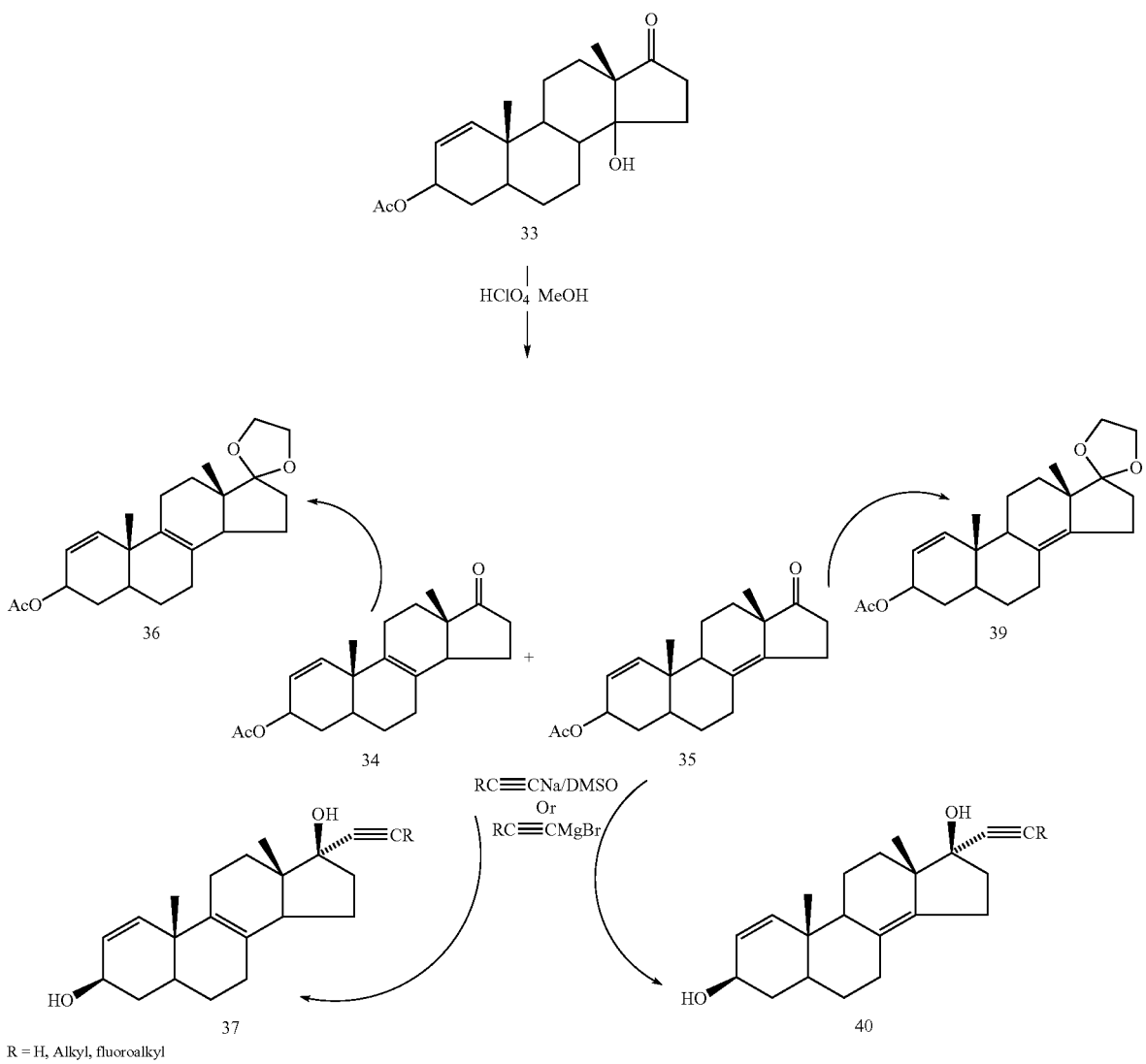
R = H, Alkyl, fluoroalkyl Scheme 10: Synthesis of 1,5,15-trienes is outlined below.
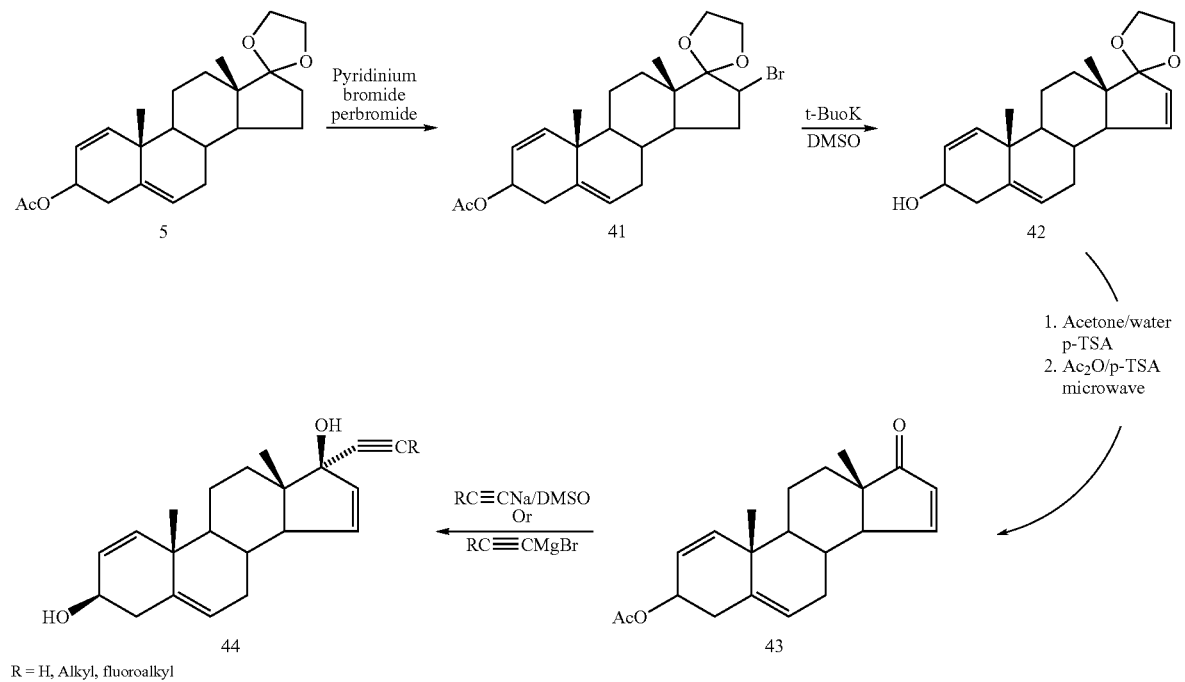
R = H, Alkyl, fluoroalkyl
Scheme 11: Synthesis of 1,5,16-trienes is outlined below.
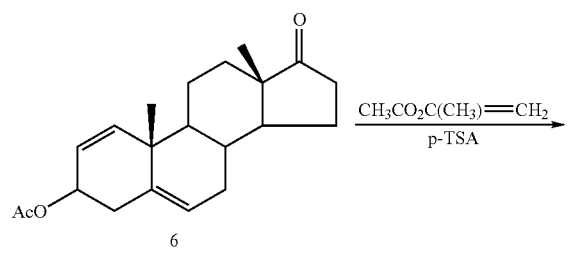
Scheme 12: Synthesis of 1,3,16-trienes is outlined below.
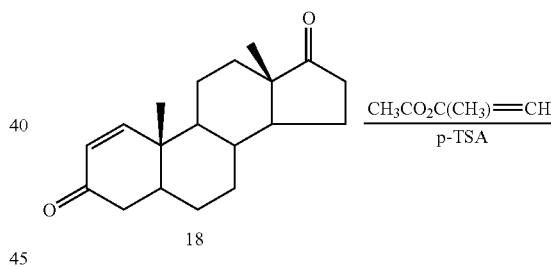
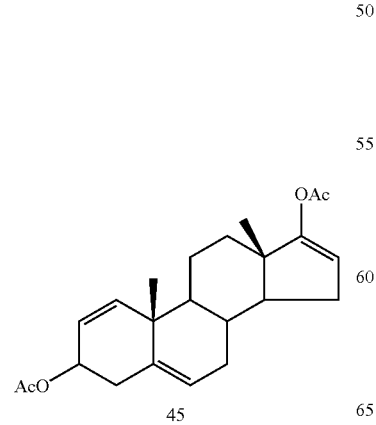
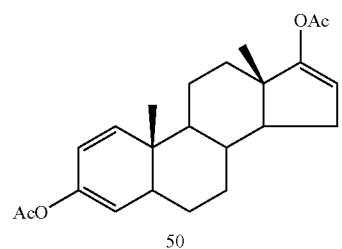

Scheme 13: Synthesis of 1,4,6-trienes is outlined below.
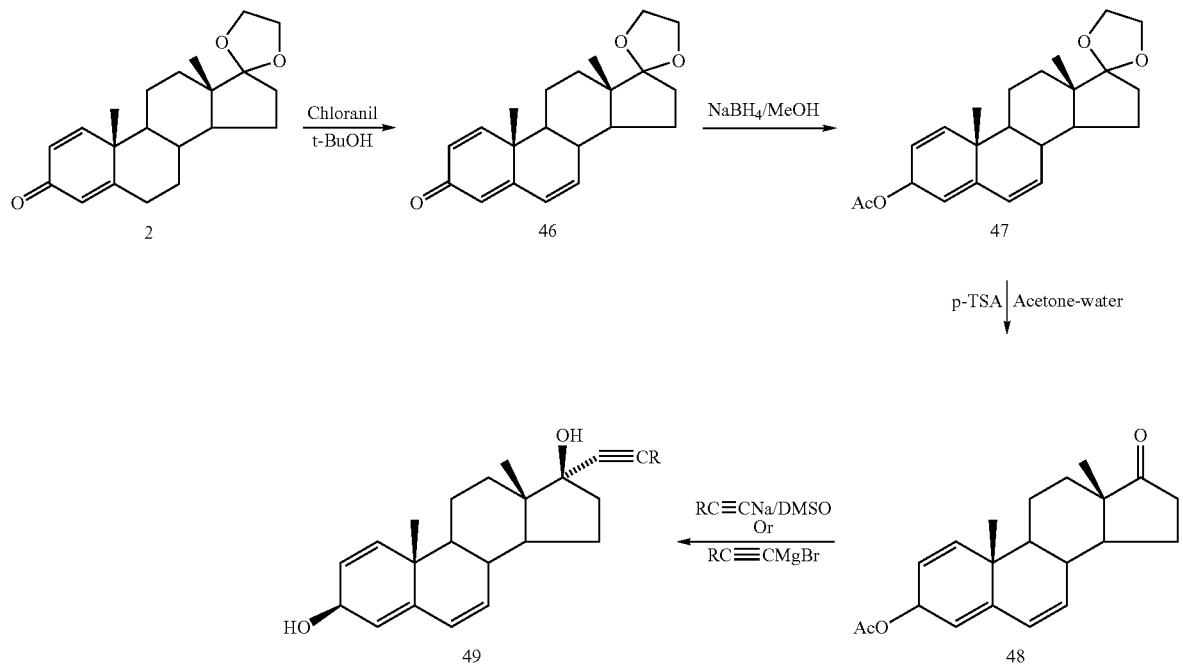
R = H, Alkyl, fluoroalkyl
Scheme 14: Synthesis of 1,8(14), 15-trienes is outlined below.
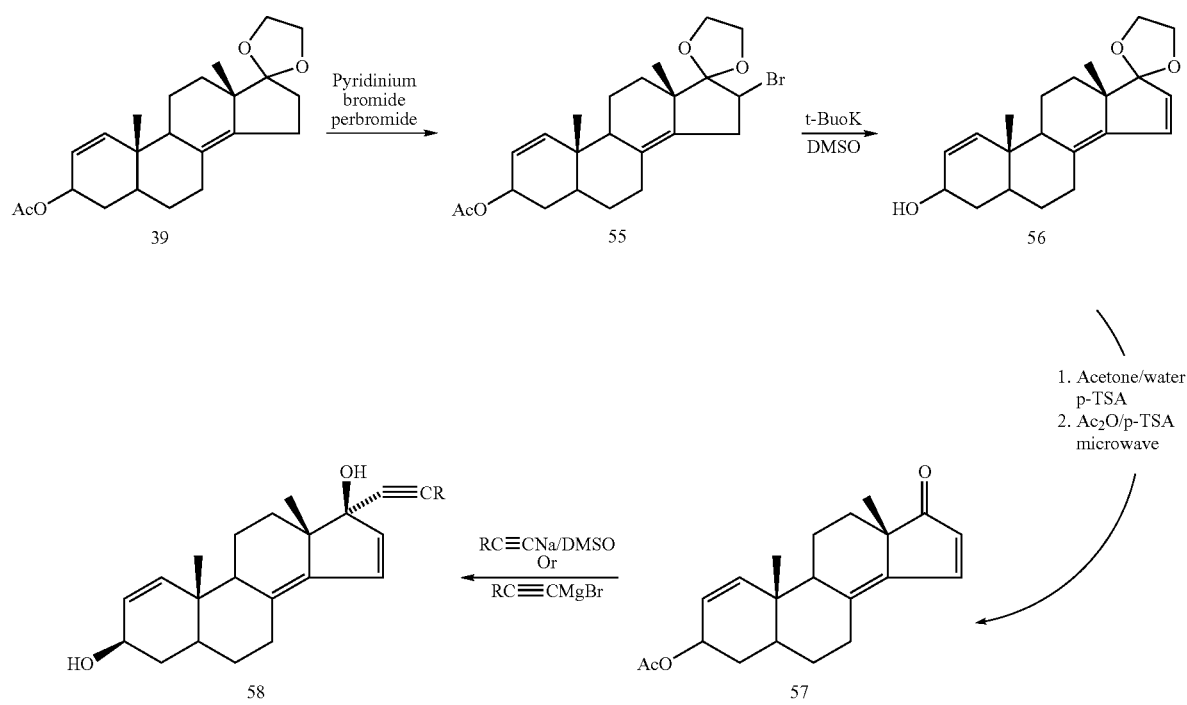
R = H, Alkyl, fluoroalkyl Scheme 15: Synthesis of 1,8(9), 15-trienes is outlined below.
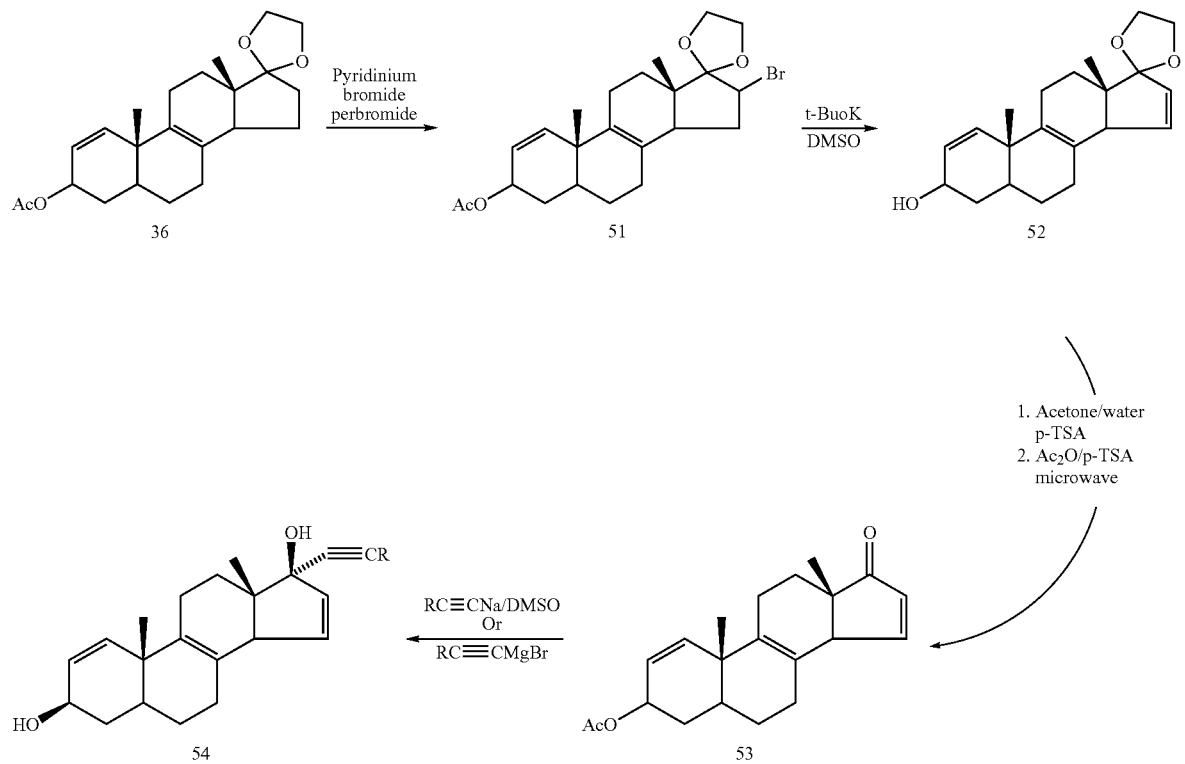
R = H, Alkyl, fluoroalkyl
Scheme 16: Synthesis of 1,5,7-trienes is outlined below.
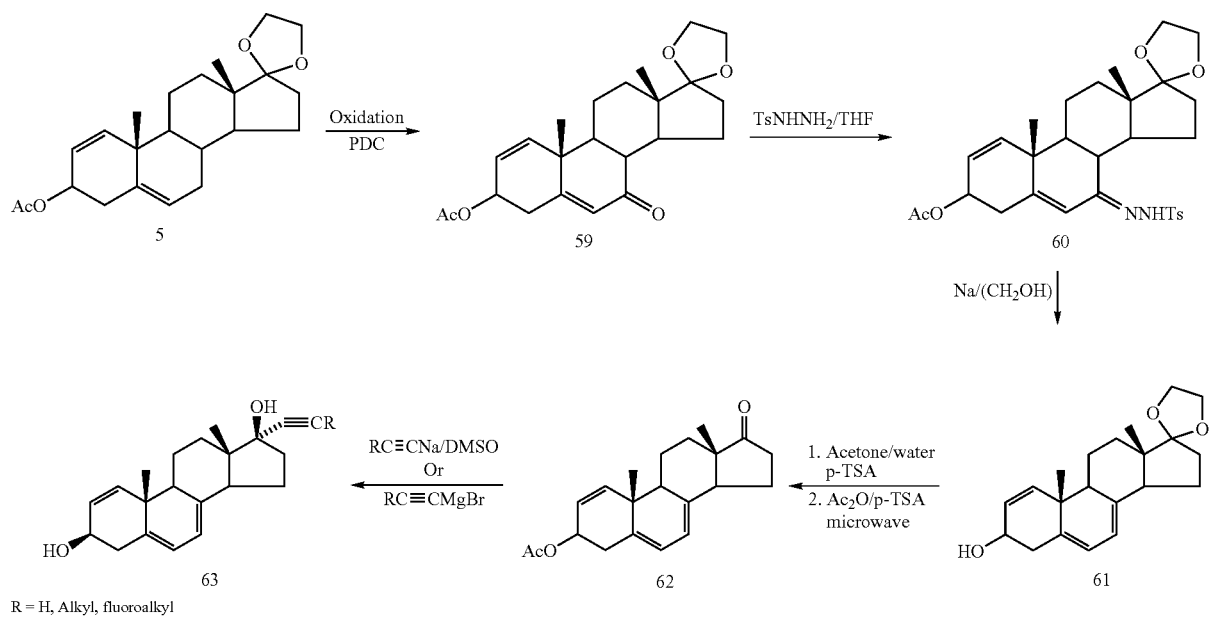
R = H, Alkyl, fluoroalkyl Scheme 17: Synthesis of 1,5,7,15-trienes is outlined below.

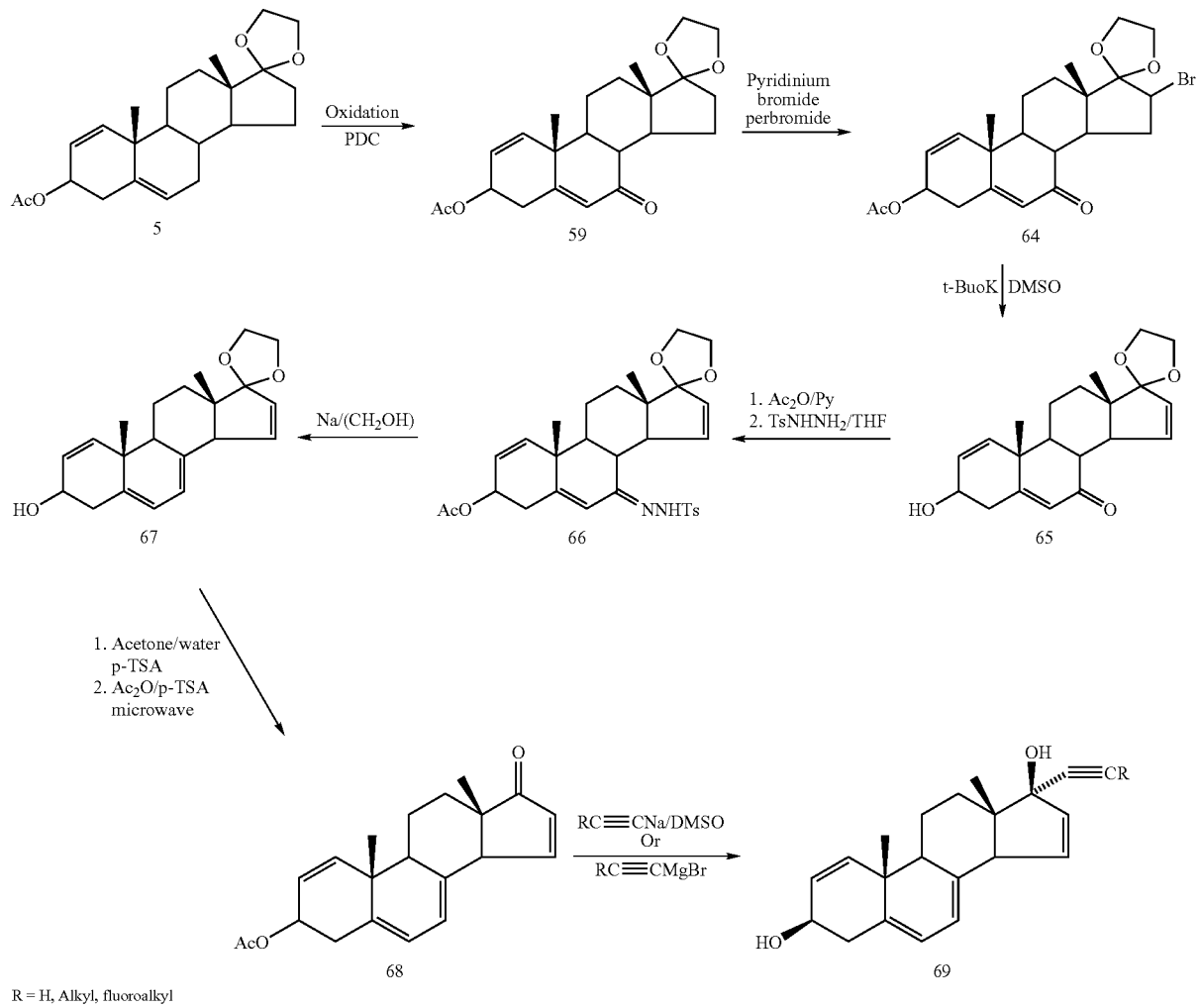

R = H, Alkyl, fluoroalkyl

The instant invention also provides for pharmaceutical compositions or formulations which may be prepared by mixing one or more compounds disclosed herein such as ADEK or compounds of structures I, II, or III, prodrugs thereof, pharmaceutically acceptable salts thereof, stereoisomers thereof, tautomers thereof, or solvates thereof, with one or more pharmaceutically acceptable carriers, excipients, binders, diluents, lubricants or the like, collectively "carriers". These compositions can be used to treat or ameliorate a variety of disorders mediated by androgen receptors. The compositions of the inventions may be used to create formulations to prevent, treat or ameliorate conditions disclosed herein such as prostrate cancer, and in particular androgen-independent prostrate cancer, as well as antiandrogen induced withdrawal syndrome. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid, liquid or gel dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration. Parenteral formulations will typically be sterile and may optionally contain a bacteriostat, e.g., EDTA or EGTA.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and/or preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective amount of a compound of the present invention may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. In general, daily dosages of about 0.1 mg/kg to about 400 mg/kg, typically about 0.5 mg/kg, about 1 mg/kg, about 4 mg/kg or about 6 mg/kg to about 10 mg/kg, about 20 mg/kg, about 40 mg/kg or about 60 mg/kg can be effective for treating humans or other mammals.

Other embodiments include use of a compound of structure I, II or II as described herein for the preparation of a medicament or for the preparation of a medicament for the prevention, treatment or amelioration of a disease or condition or to slow the progression of a disease or condition as described herein.

All references cited herein are incorporated herein by reference in their entireties.

The present invention, thus generally described, will be understood more readily by reference to the following examples, which are provided by way of illustration and are not intended to be limiting of the present invention.

EXAMPLE 1

Synthesis of 3β-acetoxy-17,17-ethylenedioxyandrosta-1,5-diene (ADEK) (5)

An exemplary synthesis method for the compound is shown below.

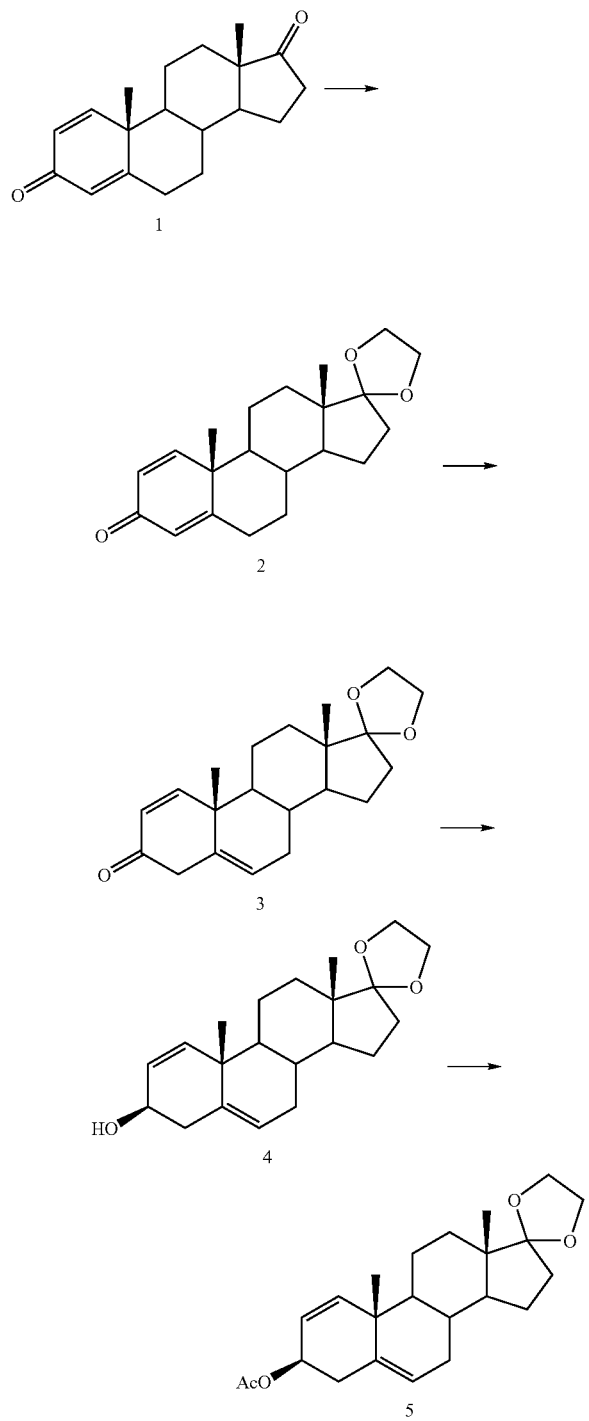

Step 1: Synthesis of 17,17-ethylenedioxyandrosta-1,4-dien-3-one (2). To a solution of androsta-1,4-dien-3,17-dione (1, 10.0 g) in benzene (600 ml) and ethylene glycol (90 ml) was added toluene-p-sulfonic acid monohydrate (0.3 g), and the solution was refluxed for 8-10 hours with a Dean-Stark apparatus for collecting water. The reaction mixture was cooled to room temperature, diluted with ethyl acetate and washed thoroughly with water, dilute sodium bicarbonate solution, water and finally with brine. The organic phase was dried over anhydrous magnesium sulfate, filtered and the organic solvent removed by rotary evaporator. The resultant solid was crystallized from methanol to give 17,17-ethylenedioxyandrosta-1,4-dien-3-one (2) as a white crystalline solid in 95% yield (11.0 g).

Step 2: Synthesis of 17,17-ethylenedioxyandrosta-1,5-dien-3-one (3). To a solution of 17,17-ethylenedioxyandrosta-1,4-dien-3-one (2, 8.5 g) in freshly distilled (over calcium hydride) dimethyl sulfoxide (160 ml) was added finely powdered potassium-t-butoxide (5.0 g), and the solution was stirred at 10° C. for 2 hours. The reaction mixture was poured into ice-water and extracted with ethyl acetate-diethyl ether (2:1 v/v). Water and the solvent employed were previously saturated with dry ice (carbon dioxide). The organic layer was washed with ice-water several times and dried over anhydrous magnesium sulfate. Evaporation of the solvent in vacuo below 35° C. gave 8.5 g of semi-crystalline solid. Recrystallization from methanol gave 17,17-ethylenedioxyandrosta-1,4-dien-3-one (3), mp. 154-57° C. The uncrystallized sample was used as such for the next step.

Step 3: Synthesis of 17,17-ethylenedioxyandrosta-1,5-dien-3β-ol (4). The crude semi-crystalline residue (3, 8.0 g) obtained above was dissolved in methanol (500 ml), and to this solution was added sodium borohydride (5.0 g) in water (100 ml) under ice cooling and stirring. After stirring for 1 hour at 0° C., the excess of sodium borohydride was decomposed by adding 400 ml of 50% aqueous acetone. After the solution stood at room temperature overnight, the deposited crystals were filtered, washed thoroughly with water and dried under vacuum. The crude product was purified by column chromatography over silica gel (eluent: ethyl acetate/petroleum ether, 1:3, v/v) and recrystallized with methanol to afford 17,17-ethylenedioxyandrosta-1,5-dien-3β-ol (4, 6.5 g). Mp. 138-140° C.

Step 4: 3β-acetoxy-17,17-ethylenedioxyandrosta-1,5-diene (5). A mixture of crude 17,17-ethylenedioxyandrosta-1.5-dien-3β-ol (4, 1.2 g) in pyridine (10 ml) and acetic anhydride (3 ml) was stirred at room temperature for 16 hours. The reaction mixture was poured into ice-water and the compound was extracted with ether. The organic layer was washed with ice-water several times followed by brine and dried over anhydrous magnesium sulfate. Evaporation of the solvent in vacuo below 35° C. gave 1.0 g of crude solid. Recrystallization from methanol gave 3β-acetoxy-17,17-ethylenedioxyandrosta-1,5-diene (5). Mp. 105-6° C.

EXAMPLE 2

An exemplary synthesis method for 3□-hydroxyandrosta-1,5-dien-17-one (7) is shown below.

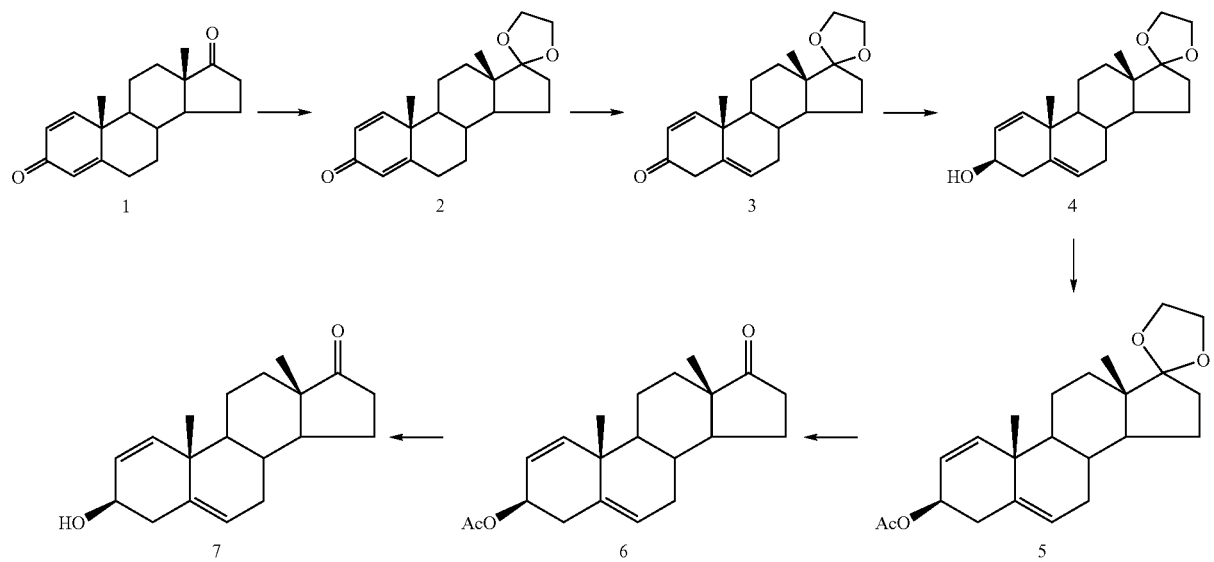

Step 1: 3β-acetoxyandrosta-1,5-dien-17-one (6). Ketal 5 (0.44 g) from Example 1 was dissolved in acetone-water (30 ml, 8:2), and treated with toluene-p-sulfonic acid monohydrate (0.1 g). After the mixture had been stirred at room temperature for 16 hr it was concentrated to half of its volume and diluted with a cold half saturated sodium bicarbonate solution. The solution was cooled, filtered to give white solid compound (0.38 g, 98%), which was further crystallized from methanol. M.p. 185-87° C., purity 99% (LC-MS).

Step 2: 3β-hydroxyandrosta-1,5-dien-17-one (7). A mixture of compound 6 (0.25 g) and potassium carbonate (0.3 g) in methanol-water (15 ml, 9:1) was stirred at room temperature for 8 hr. Solution was concentrated diluted with cold water, cooled and the precipitated solid was filtered, and crystallized from methanol. White solid, mp. 138-40° C.

EXAMPLE 3

Chemicals and Plasmids

DHT, Adiol, 17β-estradiol (E2), progesterone (P), and dexamethasone (Dex) were obtained from Sigma, Hydroxyflutamide (HF) was from Schering, and casodex was from ICI Pharmaceuticals. Other steroid compounds, derivatives of DHEA, were synthesized as above. pSG5-AR and pSG5-ARA70 were obtained as in: Yeh, S., Miyamoto, H. & Chang, C. (1997) *Lancet* 349, 852-853; Miyamoto, H., Yeh, S., Wilding, G. & Chang, C. (1998) *Proc. Natl. Acad. Sci. USA* 95, 7379-7384; Miyamoto, H., Yeh, S., Lardy, H., Messing, E. & Chang, C. (1998) *Proc. Natl. Acad. Sci. USA* 95, 11083-11088; Chang, H.-C., Miyamoto, H., Marwah, P., Lardy, H., Yeh, S., Huang, K.-E. & Chang, C. (1999) *Proc. Natl. Acad. Sci. USA* 96, 11173-11177; Yeh, S. & Chang, C. (1996) *Proc. Natl. Acad. Sci. USA* 93, 5517-5521.

Cell Culture, Transfection, and Reporter Gene Assay. The human prostate cancer cell lines, LNCaP, PC-3, and DU145, and non-prostate cancer cell line COS-1 were maintained in RPMI or Dulbecco's modified Eagle's medium (DMEM) (Life Technologies) supplemented with 10% fetal bovine serum (FBS). Transfections and luciferase (Luc) assays were performed as previously described (Miyamoto, H., Yeh, S., Wilding, G. & Chang, C. (1998) *Proc. Natl. Acad. Sci. USA* 95, 7379-7384; Miyamoto, H., Rahman, M., Takatera, H., Kang, H.-Y., Yeh, S., Chang, H.-C., Nishimura, K., Fujimoto, N. & Chang, C. (2002) *J. Biol. Chem.* 277, 4609-4617). Briefly, cells seeded to reach a density of 50-60% confluence in 12 well tissue culture plates were transfected with 1.5 µg of DNA according to "SuperFect transfection" instructions (Qiagen). After 2-3 h incubation, cells were treated with medium supplemented with charcoal-stripped FBS containing either ethanol or ligands for 24 h. The cells were then harvested and whole cell extracts were used for Luc assay. The Luc activity was determined using a Dual-Luciferase Reporter Assay System (Promega) and luminometer.

Western Blot. Western blotting analysis was performed in LNCaP cells, using monoclonal PSA antibody (DAKO), as described previously (Miyamoto, H., Rahman, M., Takatera, H., Kang, H.-Y., Yeh, S., Chang, H.-C., Nishimura, K., Fujimoto, N. & Chang, C. (2002) *J. Biol. Chem.* 277, 4609-4617). An antibody for □-actin (Santa Cruz Biotechnology) was used as the internal control. Blots were quantitated by Collage software (Fotodyne).

Ligand Binding Assay. Whole cell extracts from COS-1 with transient transfection of pSG5-AR, or LNCaP without transfection, were incubated for 2 h at 37° C. with 1 nM [³H]-synthetic androgen methyltrienolone (R1881) in the presence and absence of increasing concentrations (1-10,000 nM) of unlabeled ligands. Then, hydroxyapatite (Bio-Rad) was added and stirred for 15 min at 4° C. After centrifugation and washing, radioactivity was determined by scintillation counting.

Anti-DHT Effect of DHEA Derivatives with Low Androgenic Activity on AR Transcription. Test compounds as antiandrogenic compounds, were characterized by analysis of their ability to induce AR transcriptional activity in the AR-negative PC-3 cell line. The Luc activity was determined in the cell extracts with transient transfection of wild-type AR plasmid and androgen response element-reporter plasmid (mouse mammary tumor virus (MMTV)-Luc). After transfection, the cells were treated with various compounds at 0.1-1,000 nM. Of 17 compounds tested, only four (No. 5: 3β,7α,17β-trihydroxyandrost-5-ene; No. 10: ADEK; No. 14: 3β-acetoxyandrost-1,5-diene-17-one; and No. 16: 3β-hydroxyandrost-1,5-diene-17-one) at 1000 nM showed marginal induction on AR transcription, as compared to mock treatment.

Compounds 5, 10, 14 and 16 were characterized for their anti-DHT activity on AR transcription in PC-3 cells. Cells were transfected with AR plasmid and MMTV-Luc reporter in the presence of 1 nM DHT and each of these compounds at 0.01, 0.1, or 1 μM. While compounds No. 5, No. 14, and No. 16 showed modest suppression on DHT-induced AR transactivation, ADEK suppressed it to 30% in a dose-dependent manner. Some compounds, 3β-acetoxy-17β-hydroxyandrost-1,5-diene, 7α-hydroxyandrost-5-ene-3,17-bis ethylene ketal, 7β,17β-dihydroxyandrost-5-ene-3-ethylene ketal, 3β,16α-bis-carbomethoxyandrost-5-ene-7,17-dione, 3β,17β-dihydroxyandrost-4-ene and androst-1,4-diene-3,17-dione, were less effective in inhibiting DHT-induced AR transactivation. Other compounds, 3β,7α,17β-trihydroxyandrostane, 16α-bromoepiandrosterone, 3β,7β,17β-trihydroxyandrost-5-ene, 3β-hydroxy-5α-androstane-17-one, 7α-hydroxyandrost-5-ene-3,17-bis ethylene ketal, 17β-acetoxyandrost-4-ene-3,6-dione and 17β-propionony-7-oxoandrost-5-en-3-ethylene ketal, had little or no capacity to inhibit DHT-induced AR transactivation.

To accomplish these studies, PC-3 cells were transfected with the wild-type AR expression plasmid pSG5-AR and MMTV-Luc. After transfection, cells were cultured for 24 h with 1 nM DHT or 1,000 nM of various DHEA derivatives. The Luc activity is presented relative to that in the presence of DHT (set as 100%). The Luc activity was measured relative to that of ethanol treatment (set as 1-fold). Values from the mean ±SD of at least three determinations were used. PC-3 cells were transfected with the pSG5-AR and MMTV-Luc. After transfection, cells were cultured for 24 h with various concentrations of compounds No. 5, 10 (ADEK), 14, or 16 in the presence of 1 nM DHT. The Luc activity was determined relative to that in the presence of DHT (set as 100%). Values from the mean ±SD of at least three determinations were obtained.

ADEK was further investigated, using different cell lines and different reporters, and was also compared to non-steroidal antiandrogens, HF and casodex. ADEK had lower androgenic activity on wild-type AR transcription than HF and casodex in COS-1 cells. ADEK at 1 μM suppresses DHT-induced wild-type AR transcription to 21%, similar to the suppression by HF and casodex. In LNCaP cell line, 10 μM HF acts as full agonist, and therefore shows no suppression of DHT-induced mutant AR transcription, consistent with the previous findings (Kuil, C. W. & Mulder E. (1996) *Endocrinology* 137, 1870-1877; Miyamoto, H. & Chang, C. (2000) *Int. J. Urol.* 7, 32-34). Casodex and ADEK exhibited dose-dependent suppression to 22% and 17%, respectively, and androgenic activity of ADEK was lower than that of casodex. Similar results were obtained when MMTV-Luc was replaced with PSA-Luc. In addition, one of the AR coactivators, ARA70, which has been shown to enhance significantly agonist activity of antiandrogens (5-12 fold) (Yeh, S., Miyamoto, H. & Chang, C. (1997) *Lancet* 349, 852-853; Miyamoto, H., Yeh, S., Wilding, G. & Chang, C. (1998) *Proc. Natl. Acad. Sci. USA* 95, 7379-7384), marginally enhanced AR transactivation in the presence of ADEK (<2-fold) in DU145 cells. The results indicated that ADEK acts as a potent antagonist on DHT-enhanced transactivation of both wild-type AR and a mutant AR. Several compounds related to ADEK, i.e., 3β-acetoxyandrosta-1,5-dien-17-one, androsta-1,4-dien-3,17-dione, 3β-hydroxyanrosta-1,5-dien-17-one and 3β-acetoxy-17β-hydroxyandrosta-1,5-dien, did not show significant antagonistic effects. The agonist effect of ADEK was marginal and lower than that of non-steroidal antiandrogens. Because of this, there is less possibility of inducing withdrawal response in prostate cancer patients when using compounds such as ADEK.

The effects of ADEK on the DHT-induced transcriptional activity of AR was examined in COS-1 or LNCaP cells transfected with MMTV-Luc. The pSG5-AR was co-transfected in COS-1 cells. After transfection, cells were cultured for 24 h in the presence or absence of 1 nM DHT or various concentrations of HF, casodex, or ADEK. Luc activity was analyzed relative to Luc activity in the presence of DHT (set as 100%). Values were obtained from the mean ±SD of at least three determinations. DU145 cells were transfected with the pSG5-AR and MMTV-Luc in the presence or absence of pSG5-ARA70. After transfection, cells were cultured for 24 h with various concentrations of HF, casodex, or ADEK. The Luc activity is presented relative to that of ETOH treatment without ARA70 (set as 1-fold). Values were obtained for the mean ±SD of at least three determinations. For COS-1 cells, relative Luc activity in 1 μM ADEK was 21% of the level relative to the DHT control (100%), while Luc activity in 0.1 μM ADEK and 0.01 μM respectively was about 60% and about 75% of the control level.

EXAMPLE 4

Anti-DHT Effect of ADEK on PSA Expression and Cell Proliferation

The PSA is an AR responsive gene and presently the most useful tumor marker to monitor prostate cancer progression. The capacity of ADEK to modulate PSA expression in prostate cancer cells was tested. The Western blotting assay showed that DHT increased endogenous PSA expression in LNCaP cells to 4.3-fold over mock treatment and that ADEK and casodex decreased DHT-induced PSA expression to 49% and 58%, respectively. HF induces PSA expression to 3.5-fold, whereas ADEK and casodex increase it to less than 2-fold. The effect of ADEK on cell growth of LNCaP was tested. DHT significantly increased cell growth, and ADEK and casodex antagonized this DHT effect. ADEK and casodex marginally increased growth in the absence of androgen. These results confirm the AR transcription data and suggest that ADEK can inhibit androgen-AR-mediated prostate cancer progression.

To accomplish the PSA expression analysis, cell extracts from LNCaP cells cultured for 48 h with 1 μM HF, 1 μM casodex, or 1 μM ADEK in the presence or absence of 1 nM DHT, were analyzed on Western blots using an antibody to the PSA. The 33-kDa protein was quantitated. β-Actin expression was used as an internal control. The normalized expression level in the DHT treated cells was set as 100%. The mean ±SD of three separate experiments was determined. To determine the effect on LNCaP cell growth, the cells were cultured with 1 μM HF, 1 μM casodex, or 1 μM ADEK in the presence or absence of 1 nM DHT. Total cell number was counted by hemocytometer. The mean of at least three determinations was determined.

EXAMPLE 5

Interruption of Androgen Binding to the AR by ADEK

Clinically available antiandrogens have an affinity for the AR, allowing a competition with androgens for binding. To determine whether ADEK has this common feature of AR antagonists, the competitive androgen binding assay was performed. The affinity of ligands for the AR was assessed by incubating whole cell extracts of LNCaP or COS-1 with transfected wild-type AR with 1 nM [$^3$H]-R1881 in the presence of various concentrations (1-10,000 nM) of unlabeled DHT, HF, casodex, or ADEK. As described previously (Schuurmans, A. L. G., et al. (1988) Int. J. Cancer 42, 917-922), the relative binding affinity (RBA) values were calculated from the constructed competitive binding curves as the ratio of concentration of unlabeled ligand and concentration of DHT required to inhibit [$^3$H]-R1881 binding by 50% (Table 1 below). Competitive RBAs in LNCaP cells were DHT>casodex>HF>ADEK. Similar results were obtained in wild-type AR transfected COS-1 cells, although the RBAs are lower and binding of all the compounds in competition with [$^3$H]-R1881 was weaker. These results confirm that ADEK also competes significantly with androgen for AR binding.

TABLE 1

| Ligand | RBA in LNCaP | RBA in COS-1 with AR |
|---|---|---|
| DHT | 100.0 | 100.0 |
| HF | 23.0 | 17.1 |
| Casodex | 36.4 | 25.5 |
| ADEK | 11.1 | 6.0 |

EXAMPLE 6

Anti-Adiol Effect of ADEK on AR Transcription

Adiol, which is produced from DHEA and which can be converted to testosterone, possesses intrinsic androgen activity. Among androgens it is unique in that both HF and casodex failed to block significantly Adiol-induced AR transactivation in prostate cancer cells. Because castration with or without combination therapy with antiandrogen, decreases the serum concentration of Adiol by only 40-50% (Bélanger, et al. (1986) J. Clin. Endocrinol. Metab. 62, 812-815; Labrie, F., et al. (1988) Br. J. Urol. 61, 341-346), previous findings suggested that current CAB treatment might be insufficient to block Adiol's action in AR-positive prostate cancer. Therefore, the capacity of ADEK to inhibit Adiol-induced AR transcription was analyzed by measuring MMTV-Luc activity. The wild-type AR expression plasmid pSG5-AR was co-transfected in PC-3 cells to permit assay of Adiol-induced AR transcription. After transfection, cells were cultured for 24 h in the presence or absence of 2.5 nM Adiol and 1 µM HF, 1 µM casodex, or 1 µM ADEK. Adiol at 2.5 nM increased AR transcriptional activity in PC-3 and LNCaP to 4.5-fold and 2.8-fold, respectively, over mock treatment. ADEK at 1 µM repressed Adiol-induced AR transcription by about 43% and 58% in PC-3 and LNCaP, respectively, whereas HF at 1 µM and casodex at 1 µM failed to significantly block Adiol-induced AR transcription. These results support the conclusion that ADEK can suppress AR transactivation induced by classic androgens as well as by adrenal androgen. In these assays, Luc activity was presented relative to that in the presence of Adiol (set as 100%). Values were obtained from the mean ±SD of at least three determinations. Other test compounds, e.g., compounds of structure I, II or III, can be characterized for their capacity to modulate or antagonize adiol-induced AR transcription, or transcription induced by other AR modulators, in essentially the same manner using this assay or a suitable variation of this assay, e.g., use of adiol at other concentrations such as 1, 2, 3, 4 or 5 nM.

EXAMPLE 7

Steroid Hormone Specificity of ADEK

To characterize the steroid hormone activity of ADEK, PC-3 cells were transfected with steroid receptor/reporter (progesterone receptor (PR)/MMTV-Luc, glucocorticoid receptor (GR)/MMTV-Luc, or estrogen receptor (ER)/ERE-Luc) and analyzed for expression of the Luc reporter gene. After transfection, the cells were cultured for 24 h in the presence or absence of ligand (10 nM DHT, 10 nM progesterone, 10 nM dexamethasone, or 10 nM 17β-estradiol) or ADEK at 0.01 mM, 0.1 mM and 1.0 mM. The Luc activity was measured relative to that of ETOH treatment (set as 1-fold). Values were obtained from the mean ±SD of at least three determinations. The results indicated that ADEK had some estrogenic activity, but ADEK had no significant progesterone, glucocorticoid activity or androgenic activity.

What is claimed is:

1. A method to treat prostate cancer in a subject in need thereof, comprising administering an effective amount of a compound having the structure

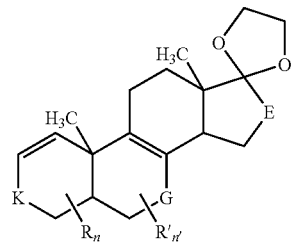

wherein

E is —C(O)— or —CR$^5$R$^6$—;

G is —CR$^3$R$^4$—;

K is —CR$^1$R$^2$—;

R$^1$ is —OR$^{11}$

R$^2$ is —H, lower alkyl or substituted lower alkyl;

R$^3$ and R$^5$ independently are —H, —OH or lower alkyl;

R$^4$ and R$^6$ independently are —H or lower alkyl;

R$^{11}$ is —H, alkyl or substituted alkyl, —C(O)—R$^{12}$, —S(O)$_{0-2}$—R$^{12}$ or —C(O)—OR$^{12}$;

R$^{12}$ is —H, alkyl or substituted alkyl;

R is —OH or unsubstituted lower alkoxy;

R' is —F or unsubstituted lower alkyl;

n is 0 or 1; and n' is 0 or 1.

2. The method of claim 1 wherein the compound has the structure
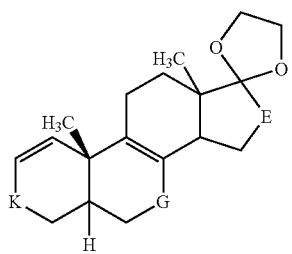
wherein $R^2$ is —H;
$R^3$ and $R^5$ are independently —H or —OH;
$R^4$ and $R^6$ are —H;
$R^{11}$ is —H, alkyl or —C(O)—$R^{12}$.
3. The method of claim 2 wherein $R^1$ is —OH or —OC(O)—$R^{12}$.
4. The method of claim 3 wherein the compound has the structure
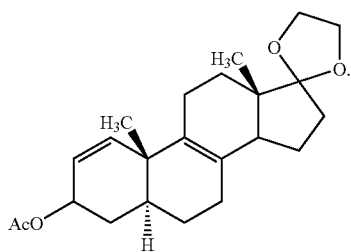
* * * * *